US011141373B2

(12) United States Patent
Cornell et al.

(10) Patent No.: US 11,141,373 B2
(45) Date of Patent: Oct. 12, 2021

(54) NATURAL SKIN CARE COMPOSITIONS AND METHODS FOR TREATING OXIDATIVE STRESS AND RESTORING SKIN HEALTH

(71) Applicant: CODEX BEAUTY CORPORATION, Portola Valley, CA (US)

(72) Inventors: Marc Cornell, Cork (IE); Barbara A. Paldus, Portola Valley, CA (US); Jorge Iván Sanhueza Sepúlveda, Santiago (CL)

(73) Assignee: CODEX BEAUTY CORPORATION, Portola Valley, CA (US)

(*) Notice: Subject to any disclaimer, the term of this patent is extended or adjusted under 35 U.S.C. 154(b) by 0 days.

(21) Appl. No.: 17/166,503

(22) Filed: Feb. 3, 2021

(65) Prior Publication Data

US 2021/0154132 A1 May 27, 2021

Related U.S. Application Data

(63) Continuation-in-part of application No. 16/901,875, filed on Jun. 15, 2020.

(60) Provisional application No. 62/861,739, filed on Jun. 14, 2019.

(51) Int. Cl.

| A61K 36/00 | (2006.01) |
|---|---|
| A61K 8/9789 | (2017.01) |
| A61K 8/9794 | (2017.01) |
| A61Q 19/08 | (2006.01) |
| A61Q 17/00 | (2006.01) |
| A61K 8/368 | (2006.01) |
| A61K 8/34 | (2006.01) |
| A61Q 19/00 | (2006.01) |
| A61K 8/99 | (2017.01) |

(52) U.S. Cl.
CPC ............ *A61K 8/9789* (2017.08); *A61K 8/345* (2013.01); *A61K 8/368* (2013.01); *A61K 8/9794* (2017.08); *A61K 8/99* (2013.01); *A61Q 17/00* (2013.01); *A61Q 19/007* (2013.01); *A61Q 19/08* (2013.01)

(58) Field of Classification Search
None
See application file for complete search history.

(56) References Cited

U.S. PATENT DOCUMENTS

| 4,933,177 | A | 6/1990 | Grollier et al. |
|---|---|---|---|
| 7,678,768 | B2 | 3/2010 | Purpura et al. |
| 10,300,012 | B2* | 5/2019 | Gatto ............... A61P 27/16 |
| 10,721,937 | B1 | 7/2020 | Cornell et al. |
| 2006/0013839 | A1 | 1/2006 | Yu |
| 2009/0028969 | A1* | 1/2009 | Sene ................. A61K 8/602 424/757 |
| 2014/0017344 | A1 | 1/2014 | Letelier Munoz et al. |
| 2014/0128333 | A1 | 5/2014 | Hancke Orozco et al. |

FOREIGN PATENT DOCUMENTS

| EP | 3398607 A1 | 11/2018 |
|---|---|---|
| GB | 2485483 A | 5/2012 |
| WO | 2006032091 A2 | 3/2006 |
| WO | 2013149323 A1 | 10/2013 |
| WO | 2014085946 A1 | 6/2014 |
| WO | 2019002714 A1 | 1/2019 |

OTHER PUBLICATIONS

Avello et al, Antioxidants and antimicrobial extracts of Aristotelia chilensis and Ugni molinae and its applications as preservatives in cosmetic products. Boletin Latinoamericano y del Caribe de Plantas Medicinales y Aromaticas (2009), vol. 8, No. 6, pp. 479-486 (Year: 2009).*
Bradford, "A Rapid and Sensitive Method for the Quantitation of Microgram Quantities of Protein Utilizing the Principle of Protein-Dye Binding," Analytical Biochemistry, vol. 72, Jan. 29, 1976, pp. 248-254.
Backhouse et al., "Analgesic, Anti-Inflammatory and Antioxidant Properties of Buddleja globosa, Buddlejaceae," Journal of Ethnopharmacology, vol. 116, Nov. 22, 2007, pp. 263-269.
Dawane et al., "Experimental Evaluation of Anti-Inflammatory Effect of Topical Application of Entada Phaseoloides Seeds as Paste and Ointment," North American Journal of Medical Sciences, Nov. 31, 2011, pp. 513-517.
Lim et al., "NADPH Oxidase is a Novel Target of Delphinidin for the Inhibition of UVB-Induced MMP-1 Expression in Human Dermal Fibroblasts," Experimental Dermatology, vol. 22, Apr. 18, 2013, pp. 417-437.
Puri et al., "Effects of Air Pollution on the Skin: A Review," Indian Journal of Dermatology, Venereology, and Leprology, vol. 83, Issue 4, Jul.-Aug. 2017, pp. 415-423.

(Continued)

*Primary Examiner* — Qiuwen Mi
(74) *Attorney, Agent, or Firm* — Medler Ferro Woodhouse & Mills

(57) ABSTRACT

Compositions intended for application onto human skin damaged by oxidative stress can include (1) a mixture of at least: (a) a leaf extract of *Aristotelia chilensis*; (b) a leaf extract of *Buddleja globosa*; (c) a leaf extract of *Ugni molinae*; (d) optionally, a bark/seed extract of *Entada phaseoloides*; (e) optionally, a blend of *Pfaffia paniculata, Ptychopetalum olacoides*, and *Lilium candidum* extracts; and (f) at least one humectant; (2) an emulsifier; and (3) a dermatologically acceptable carrier, wherein (a)-(f) are employed in amounts sufficient to synergistically neutralize existing free radicals present in the skin, while proactively priming the skin by repairing and/or protecting its *Stratum corneum* without unduly impairing the *Stratum corneum*'s acid mantle, and wherein the composition is natural, free of a skin-sensitizing amount of an essential oil, and has a pH ranging from about 4.5 to about 5.5.

14 Claims, 3 Drawing Sheets

(56) References Cited

OTHER PUBLICATIONS

Lopez et al., "Murta (Uqni molinae Turcz) A Review on Chemical Composition, Functional Components and Biological Activities of Leaves and Fruits," Chilean Journal of Agricultural and Animal Sciences, vol. 34, No. 1, Oct. 31, 2017, pp. 43-56.
Araviiskaia et al., "The Impact of Airborne Pollution on Skin," Journal of the European Academy of Dermatology and Venereology, vol. 33, Aug. 31, 2019, pp. 1496-1505.
Parrado et al., "Environmental Stressors on Skin Aging. Mechanistic Insights," Frontiers in Pharmacology, vol. 10, Article 759, Jul. 9, 2019, pp. 1-17.
Ryu et al., "Particulate Matter Induces Inflammatory Cytokine Production via Activation of NFkB by TLR5-NOX4-ROS Signaling in Human Skin Keratinocyte and Mouse Skin," Redox Biology, vol. 21, Dec. 15, 2018, 16 Pages.
Liao et al., "The Impact of Particulate Matter (PM2.5) on Skin Barrier Revealed by Transcriptome Analysis: Focusing on Cholesterol Metabolism," Toxicology Reports, vol. 7, Nov. 25, 2019, pp. 1-9.
Schikowski et al., "Air Pollution and Skin Aging," Current Environmental Health Reports, vol. 7, Jan. 11, 2020, pp. 58-64.
Backhouse et al., "Antinociceptive Activity of Buddleja Globosa (Matico) in Several Models of Pain," Journal of Ethnopharmacology, vol. 119, Jun. 28, 2008, pp. 160-165.
Suwalsky et al., "Human Erythrocytes are Affected In Vitro by Flavonoids of *Aristotelia chilensis* (Maqui) Leaves," International Journal of Pharmaceutics, vol. 363, Jul. 16, 2008, pp. 85-90.
Arancibia-Avila et al., "Partial Characterization of a New Kind of Chilean Murtilla-like Berries," Food Research International, vol. 44, Jan. 5, 2011, pp. 2054-2062.
Vidal et al., "Microencapsulation of Maqui (*Aristotelia chilensis* [Molina] Stuntz) Leaf Extracts to Preserve and Control Antioxidant Properties," Chilean Journal of Agricultural Research, vol. 73, Issue 1, Jan. 1, 2013, 8 Pages.
Avello et al., "Antioxidant and Antimicrobial Extracts of Aristotelia Chilensis and Ugni Molinae and their Applications as Preservatives in Cosmetic Products," Latin American and Caribbean Bulletin of Medicinal and Aromatic Plants, vol. 8, No. 6, Jan. 1, 2019, 14 Pages.
International Search Report and Written Opinion from PCT Application No. PCT/US2020/037756, dated Sep. 10, 2020.
Non-final Office Action in U.S. Appl. No. 17/189,553, dated Jun. 17, 2021.

* cited by examiner

NATURAL SKIN CARE COMPOSITIONS AND METHODS FOR TREATING OXIDATIVE STRESS AND RESTORING SKIN HEALTH

RELATED APPLICATIONS

This is a continuation-in-part application of application Ser. No. 16/901,875 filed Jun. 15, 2020, which claims priority to U.S. Provisional Application No. 62/861,739, filed Jun. 14, 2019, the entire contents of both being hereby incorporated by reference.

FIELD OF THE INVENTION

The present disclosure generally relates to compositions and methods for treating skin suffering from oxidative stress. More particularly, the disclosure is directed to the use of specific associations of botanical extracts and preservative systems to arrive at compositions and methods of enhancing the antioxidant defense potential, hydration, and barrier effect of skin suffering from oxidative stress.

BACKGROUND

Skin is subject to damage by a number of extrinsic (environmental) and intrinsic factors. Examples of extrinsic factors include exposure to ultraviolet (UV) rays emanating from the sun, as well as harmful chemical agents found in airborne pollution such as smog and cigarette smoke. Intrinsic factors that negatively impact skin include, for example, chronological aging, a person's genetic makeup, and other biological changes that occur from within the skin. These factors cause skin to experience deleterious cellular effects associated with oxidative stress caused by harmful free radicals in the skin. Some of the most common free radicals are included within a group of reactive compounds termed reactive oxygen species (ROS). The three primary species of ROS include the superoxide anion ($O_2^{\cdot-}$), hydrogen peroxide ($H_2O_2$), and the hydroxide radical ($HO^{\cdot}$).

$O_2^{\cdot-}$ and $HO^{\cdot}$ are commonly referred to as "free radicals." They can react with organic substrates and lead to intermediate species able to further produce other ROS. For instance, H atom abstraction by $HO^{\cdot}$ free radicals on a C—H bond leads to a carbon-centered radical, that further rapidly reacts with $O_2$ to give a peroxyl radical $RO_2^{\cdot}$. The latter may react with another substrate to give a new carbon-centered radical and a hydroperoxide ROOH, which may decompose into an alkoxyl radical RO in a reaction catalyzed by redox competent metal cations such as iron or copper (e.g., as occurring with heme proteins). These "secondary" species are all ROS and share a similarity in structure and reactivity with the three primary species $O_2^{\cdot-}$, $H_2O_2$, and $HO^{\cdot}$.

Many individuals purposefully expose their skin to harmful UV radiation by sunbathing or using tanning beds in an effort to obtain a suntan, considered by many to be a sign of beauty and affluence. Unfortunately, although the immediate effects of ultraviolet radiation may be considered aesthetically and socially gratifying, the long-term hazards including the risk of oxidative stress are cumulative and potentially quite serious, as is evidenced by the size of the global sunscreen market. This market has grown considerably in recent years, with many new products being introduced each and every year. What used to be considered a seasonal business is now viewed as one requiring year-round attention. Sun protection actives, meant to absorb and/or reflect harmful UV rays, are now included in a wide variety of personal products, particularly cosmetic products meant to be worn daily.

For example, many cosmetics include compounds that prevent or combat the premature aging of skin, a phenomenon termed photoaging. Photoaging is characterized by wrinkling and yellowing of the skin, along with other physical changes such as cracking, telangiectasia (spider vessels), solar keratosis (growths), ecchymoses (subcutaneous hemorrhagic lesions), and loss of elasticity (sagging). It results from repeated exposure to UV light. Usually, the primary short-term hazard of prolonged exposure to UV light is erythema, i.e., sunburn. UV rays with wavelengths in the 290-320 nm range, designated as UVB rays, tend to be the primary cause of erythema. While UVA rays (320-400 nm) is also known to cause erythema, UVB rays are known to play a significant role in photoaging due to their ability to penetrate more deeply into the skin and cause free-radical formation throughout the epidermal and dermal layers.

Exposure to UV radiation is known to cause direct DNA damage within skin cells and can additionally lead to forms of indirect DNA damage through ROS generation. In addition to causing DNA damage, ROS generated by UV exposure can damage other components of the cell (e.g., proteins, lipids, and organelles). Sufficient DNA damage or even an excess in the cellular levels of ROS can initiate apoptosis, a form of programmed cell death, and/or an inflammatory response. ROS and other free radicals are generated during inflammation and can further impact the health and homeostasis of the skin. For example, during this cascade of events, enzymes are activated in the skin to break down collagen. Taken together, the direct DNA damage and ROS generation caused by UV exposure contribute to photoaging.

Regarding other environmental aging factors such as air pollution like smog and cigarette smoke, chemicals present therein are either themselves free radicals such as, for example, nitrogen dioxide ($^{\cdot}NO_2$), or have the ability to drive free-radical formation. These free radicals, when present within a biological setting such as the skin, react with organic and inorganic compounds, often perverting their structure/function in a deleterious way. The importance of this process lies in the reactivity of the molecules involved.

Under normal conditions, electrons orbit around atomic nuclei within distinct spatial orbitals that are arranged within groups of hierarchically-ordered electron shells. The number and type of orbitals increases with increasing atomic number, filling in various electron shells. In general, a "full" orbital consists of a pair of electrons having opposite spins and results in a stable or non-reactive orbital. When an atom has an orbital that is partially filled, particularly in the valence shell, the single unpaired electron encourages chemical reactivity. This is common to many elements and is the impetus for the formation of larger compounds from discrete elements. However, in the case of free radicals like ROS, the additional electron creates a reactive inorganic compound that is potentially very dangerous because it can react indiscriminately with neighboring molecules such as proteins, DNA, and vital cellular structures such as the cell membrane or other organelles.

High cellular concentrations of free radicals can cause extensive cellular damage. The extent of damage depends on the availability of cellular defense mechanisms such as antioxidants or specialized enzymes that are designed to neutralize free radical reactivity (e.g., superoxide dismutase and peroxidases). These cellular defense mechanisms help reduce the amount of damage free radicals and other reactive species may cause to the skin by scavenging free radicals or enzymatically converting the free radicals to a less toxic compound. The body's antioxidant defense system can become impaired, however, by the aging process and/or compromised by, for example, inflammation, erythema, infection, genetic predisposition, or other disorders affecting the generation of or response to oxidative stress.

Oxidative stress has also been found to negatively impact water homeostasis of the skin, i.e., the ability of the skin to maintain consistent hydration levels. It is important to the health and appearance of skin to keep it properly hydrated and nourished—counteracting the damage caused by oxidative stress. Dry skin is a particularly common disorder that affects both males and females equally and is particularly prevalent in older individuals and those genetically predisposed to such a condition. People suffering from dry skin complain of flaking, itching, irritation, and an overall dull, rough, and lackluster appearance to their skin.

Moreover, as a person ages, their skin tends to produce fewer natural oils that aid in preventing moisture from escaping from, and thus dehydrating, the skin. Disruption of water homeostasis occurs at an early stage as a person's skin ages. This is, in part, because the expression of aquaporin-3, one of the proteins that regulates water flow at a cellular level, decreases as a person ages. Skin lacking proper hydration cannot communicate nutrients throughout the organ for proper cellular maintenance. Further, hydration status regulates sodium flux and inflammatory pathways in the skin, and when dehydrated, the skin becomes irritated and inflamed. Thus, by maintaining good hydration of the epidermis, particularly the outermost layer of epidermal cells called the *Stratum corneum* (aka the horny layer), inflammation is reduced and less ROS is generated thereby. This enhances the effectiveness of endogenous antioxidant molecules, as well as cosmetic agents exhibiting antioxidant properties, to help alleviate or respond to oxidative stresses and free radical formation. In particular, properly hydrated skin slows photoaging by helping to maintain skin's elasticity.

As alluded to above, the skin has a strong innate antioxidant defense to protect against UV-induced oxidative stress and free radical formation. This is accomplished via a cadre of endogenous antioxidant enzymes, such as superoxide dismutase (SOD), peroxidase, and catalase, along with endogenous antioxidant compounds. Glutathione (GSH) is an exemplary cellular antioxidant that serves—in its reduced state—as the substrate for enzymatic neutralization of hydrogen peroxide to water. The resultant oxidized glutathione can be recycled back to its reduced form by an NADPH-dependent reductase, thereby allowing it to once again serve as an antioxidant. Unfortunately, excessive exposure to UV radiation can overwhelm the cutaneous antioxidant capacity, leading to oxidative damage and ultimately to immunosuppression or serious skin disorders such as photoaging and skin cancer.

The skin's barrier function is another important defense against oxidative stress. The term "barrier function" refers to the functions predominantly provided by the outermost layer of the skin, the *Stratum corneum*—a.k.a. the horny layer—which is responsible for retaining moisture within the lower layers of epidermal cells and for keeping damaging elements like UV rays, pollutants, and pathogens out. When the skin's barrier function is operating properly, skin is firm, plump, and hydrated. However, when the barrier function deteriorates or is compromised, skin health deteriorates as well.

The *Stratum corneum* is the primary line of defense between an individual and the outside world, preventing environmental chemicals and biological irritants from penetrating the skin. For example, microbes, allergens, toxic chemicals, UV light, and the like are blocked by the *Stratum corneum* from penetrating into the skin. This is typically referred to as the *Stratum corneum*'s "physical" defense mechanism.

While protection against external assaults is a very important function served by the *Stratum corneum*, an similarly important function is to prevent the escape of water. The *Stratum corneum* is made up of multiple stacks of flattened cells or corneocytes, each of which is encased in a thick coating of fat. If one were to compare the *Stratum corneum* to a brick wall, the stack of cells are bricks, and the fatty matrix encasing them is the mortar. Together, they form a barrier that keeps skin's water content inside so that the skin stays firm, hydrated, elastic, and less prone to wrinkling.

The lipid portion of the *Stratum corneum* is primarily responsible for the water-sealing properties. These lipids are comprised of various oily compounds naturally produced by the human body, including diglycerides, triglycerides, fatty acids, ceramides, cholesterol, and squalene. These lipids form a semi-permeable, waterproofing multi-layered matrix that surrounds the skin cells and provides structure to the skin barrier by holding the skin cells tightly in place.

One of the ways by which the *Stratum corneum* is oftentimes damaged involves an individual's personal skin care routine. For example, daily cleansing of the skin with cleansers having an overly alkaline pH (skin naturally has a slightly acidic pH) or containing aggressive surfactants such as sulfates, over time, wears away the corneocytes and lipid matrix of the *Stratum corneum* resulting in cracks and gaps being formed therein. This same deleterious phenomenon is observed when using anti-aging products. Many serums and cosmetic creams contain high concentrations of aggressive active ingredients meant to stimulate cell turnover and reduce the appearance of fine lines and wrinkles. Examples of such ingredients include retinols, ascorbic acid (Vitamin C), and alpha hydroxy acids such as glycolic acid. Routine application of these products leads to *Stratum corneum* damage and loss of hydration barrier function as the high potency actives wear out the integrity of the *Stratum corneum*'s skin cells and lipids.

The *Stratum corneum* can also be damaged by various extrinsic (environmental), and intrinsic factors. Examples of extrinsic factors include exposure to the aforementioned UV rays, high energy visible light (violet-blue light) emanating from TVs, computer screens, and smart phones, as well as harmful chemical agents found in airborne pollutants like car exhaust, smog, and cigarette smoke. Intrinsic factors that can negatively impact the *Stratum corneum* include, for example, chronological aging, a person's genetic makeup, and other biological changes that occur within the skin and body. These factors have deleterious cellular effects on the *Stratum corneum* due to oxidative stress caused by harmful free radicals.

More particularly, while the damage caused by UV rays in terms of sunburn, photoaging, and skin cancer have been extensively studied, UVB rays have also been found to cause damage to the *Stratum corneum* upon exposure. This is believed to be caused by delamination of the *Stratum corneum*'s lipid matrix resulting in a decrease in intercellular strength, strain, and cohesion between the corneocytes and lipids. UV exposure also naturally dries out the skin. Once the skin becomes dry and flaky, the ability of the corneocytes and lipids to form a strong, cohesive matrix is compromised, leading to cracks and gaps being formed within the *Stratum corneum* and thereby providing a pathway for pathogens to enter and water to escape.

The negative impact of ROS and other free radicals on the *Stratum corneum* is also highly problematic as previously discussed. In addition to UV-induced free radicals, air pollutants like car exhaust, smog, and cigarette smoke contain chemicals that are either themselves free radicals or can drive free-radical formation. These free radicals, when present within a biological setting such as the *Stratum corneum*, cause damage to the lipids and proteins constituting the structural components of the *Stratum corneum*. The extent of damage depends on the availability of neutralizing antioxidant cellular defenses produced by the body.

As was mentioned previously, because oxidative stress negatively impacts the ability of the skin to maintain constant hydration levels, it is important to the health and appearance of skin to keep it properly hydrated. Aside from drinking plenty of water, maintaining proper hydration levels is highly dependent on a properly functioning *Stratum corneum*. A compromised *Stratum corneum*, unable to effectively seal water within the skin, causes skin to become dry. People suffering from dry skin complain of flaking, itching, irritation, and an overall dull, rough, and lackluster appearance to their skin. Hence, while protection against external assaults is an important function served by the *Stratum corneum*, an equally important function is to prevent dry skin-inducing water loss.

Despite its importance, the barrier formed by the *Stratum corneum* is quite delicate and prone to thinning as a person ages. Moreover, any assault on the *Stratum corneum*, either from external assaults or internal deficiencies, can lead to sensitized, dehydrated skin that is susceptible to environmental harm, dryness, irritation, breakout, sagging, and other signs of aging. When skin is dry, it is more permeable to irritants and allergens that can trigger inflammation. Beyond the free radical production and consequent damage attendant to inflammatory responses in the skin, the penetrating irritants and allergens can cause rosacea, acne, eczema, and premature aging.

In view of the above, it is clear that in order to both effectively treat skin already damaged from oxidative stress and to protect against further damage by oxidative stress, at least three issues should be addressed. First, skin-resident free radicals should be neutralized to terminate ongoing damage from oxidative stress. Second, the skin should be rehydrated to restore osmotic balance, including replacement of any water/moisture lost. Lastly, the skin's barrier function should be repaired and/or restored to help protect the skin against further attack (e.g., by free radicals) stemming from both extrinsic and intrinsic factors as well as to prevent dry skin-inducing water loss.

Accordingly, there is a need for skin care compositions and methods that treat or address oxidative stress and restore skin health by neutralizing free radicals in the skin, rehydrating the skin, and repairing and/or protecting the skin's barrier function.

In addition to the above-noted physical defense mechanism of the *Stratum corneum*, the skin also possesses a "biological" defense mechanism commonly referred to as its acid mantle. The acid mantle is a thin film formed on the surface of the *Stratum corneum* and comprised of a mixture of oils produced by the body and amino acids present in sweat. The acid mantle's primary role is to maintain a healthy and diverse microbiome on the skin's surface. This diversity of bacteria, fungi, and viruses that comprise a healthy skin microbiome help to select against the colonization of potentially harmful pathogens and can drastically effect the potency and scent of body odor, among other things. Maintaining a healthy and diverse skin microbiome is also important for maximizing overall skin health and its ability to act as a biological defense mechanism for the host.

A corollary theory to the function of the acid mantle relates to its role in skin homeostasis, i.e., the interaction between cells, tissues, and organisms in the balanced maintenance and regulation of skin's biological functions. As the name implies, the skin barrier's acid mantle is acidic in nature with a pH of from about 4.5 (more typical of males) to about 5.5 (more typical for females). The acidic nature of the acid mantle is one pressure on bacterial selection and, in turn, skin homeostasis which are important elements of proper skin barrier functionality.

Accordingly, there is also a need for skin care compositions and methods that address oxidative stress, rehydrate the skin, and repair and/or protect the skin's barrier function without unduly impairing the *Stratum corneum*'s acid mantle.

There is no shortage of conventional cosmetic products in the market meant to enhance the health and appearance of skin by combatting the negative effects associated with the influence of both extrinsic and intrinsic factors. However, the cosmetic industry has recently embraced a sub-category of these products deemed to be organic/natural, and there is a current trend by consumers towards these types of goods. These products are believed to possess health and environmental benefits. In line with the philosophy of such products, consumers also expect them to be paraben-free, phthalate-free, sulfate-free, silicone-free, synthetic fragrance-free, alcohol-free, phenoxyethanol-free, or otherwise non-toxic. This category of organic/natural products has become one of the fastest growing in the global personal care and cosmetic segments.

In response to the outstanding need in the industry for products that meet certain thresholds of "natural" and "organic" ingredients, coupled with the lack of official standards for what qualifies as "natural" and "organic," preservative formulation has become a cottage industry with consumers gravitating towards products containing natural extracts, botanicals, or other ingredients derived from natural sources, while avoiding those products having ingredients that are either known to cause or suspected of causing adverse health reactions. Unfortunately, this ad hoc approach and decentralization of acquired knowledge and experience of generating effective preservative formulations has led to a host of ineffective solutions that typically result in diminished shelf-life and usability of associated cosmetic consumer products.

Various third-party certifications have been established in an attempt to bring consistency and reliability to the use of natural and organic preservatives in topical consumer products. For example, ECOCERT® is an organic certification organization based in Europe that conducts inspections in over 80 countries, making it one of the largest organic certification organizations in the world. ECOCERT® primarily certifies food and food products but also certifies cosmetics, detergents, perfumes, and textiles, and is a leading certifier of fair-trade food, cosmetics, and textiles.

Another example is the Cosmetic Organic Standard (COSMOS), a Europe-wide private standard that was developed by five charter members: BDIH (Germany), Cosmebio (France), Ecocert Greenlife SAS (France), ICEA (Italy), and Soil Association (Great Britain). They were all combined under an AISBL (international non-profit organization based in Brussels), the purpose of which was to set out minimum common requirements, harmonize organic and natural cosmetic certification rules, and lobby institutions in the sector's interests. COSMOS makes use of the principles in the ECOCERT® standard: to promote the use of ingredients from organic farming, use production and manufacturing processes that are environmentally sound and safe for human health, and include and expand the concept of "green chemicals."

The National Organic Program (NOP), a federal regulatory framework in the United States governing organic food, is yet another certification. The core mission of the NOP is to protect the integrity of the United States Department of Agriculture (USDA) organic seal. The seal is used for products adhering to USDA standards that contain at least 95% organic ingredients.

Hence, the industry has increased its efforts to develop "natural" cosmetic formulations using non-synthetic ingredients. This approach differs from the synthetic ingredient-based approach that has allowed the cosmetic industry to develop cosmetics with consistent product integrity, performance, and shelf life through the use of harsh, irritating, synthetic ingredients such as phenoxyethanol.

Accordingly, there is also a need for skin care compositions and methods for treating or addressing oxidative stress and restoring skin health that are natural and free of harsh, irritating, synthetic ingredients while providing effective broad-spectrum preservative protection as well as promoting or cooperating with ingredients for treating oxidative stress.

The use of botanical extracts on skin, in general, is known. However, based on only the sheer number of botanical extract candidates in existence, together with extraction techniques and solvents that may be used, a virtually infinitesimal number of products can be formulated with no assurance that the composition made will be both stable and useful for its desired purpose. Consequently, the ability to formulate skin treatment products, in the absence of skin-sensitizing ingredients, that are natural, highly efficacious and stable, is a daunting challenge as the inventors have discovered. One cannot merely combine a mixture of random botanical extracts, in arbitrary concentrations, using arbitrary extraction techniques and solvents, with the expectation that all of the disparate ingredients contained therein will be both compatible to one another, and yield the intended benefits and properties.

For example, U.S. Pat. No. 4,933,177 discloses the use of certain botanical ingredients for application onto skin. However, the reference is devoid of any specific teaching or suggestion regarding the precise association of ingredients, extraction techniques and solvents to be used, as well as which types of ingredients are to be avoided, in order to formulate an efficacious, natural product capable of enhancing skin health and appearance.

Similarly, U.S. Pat. No. 7,678,768; GB 2485483; WO 2006/032091; WO 2012/033422; WO 2013/149323; and WO 2019/002714 all disclose botanical ingredients for application onto skin for a plethora of potential uses. However, not only do these references disclose a small sample size of puzzle-piece candidates available to a formulator, but when one also considers the amounts in which each of these ingredients may be used, together with all the other variables that must be taken into consideration when formulating with plant extracts, to say that successfully arriving at a targeted product is like finding the proverbial needle in a haystack, is indeed an understatement.

One of the major deterrents associated with the use of botanical ingredients in skin care compositions relates to their relative instability in products as evidenced by loss of potency, odor deviations, and discoloration. These negative attributes increase the risk of microbiological contamination and proliferation, instability, and inadequate safety of the products. This problem becomes even more acute when the composition has to qualify as being "natural." The elimination of conventionally used synthetic, inorganic, and/or petroleum-derived ingredients from a formulator's toolbox severely hampers their ability to make efficacious, yet stable, skin treatment products. One might argue that a formulator skilled in the art could determine, through routine experimentation, which botanical extracts, auxiliary ingredients, excipients, solvents, and amounts of each can be combined in order to arrive at an intended product. However, as was mentioned above, in view of the sheer number of combinatorial permutations that exist, based on the number of ingredients that may be chosen, causes the successful formulation of such a product to be based more on luck and happenstance, as opposed to routine experimentation.

Based on the foregoing, it is an object of embodiments of the present disclosure to provide natural, organic and ECOCERT®-approved skin care compositions and methods that are effective at treating and priming skin damaged by oxidative stress.

Another object of embodiments of the present disclosure is to provide natural, organic, and ECOCERT®-approved compositions and methods capable of proactively priming the skin and enhancing its ability to defend against free-radical aggression.

Another object of embodiments of the present disclosure is to provide skin care compositions and methods having effective broad-spectrum anti-microbial activity using natural ingredients while treating or addressing oxidative stress and/or priming the skin against free-radical aggression.

SUMMARY

The present disclosure is directed to a composition intended for application onto human skin, the composition that includes (1) a mixture of at least: (a) a leaf extract of *Aristotelia chilensis*; (b) a leaf extract of *Buddleja globosa*; (c) a leaf extract of *Ugni molinae*; and (d) optionally, a bark/seed extract of *Entada phaseoloides*; (e) optionally, a blend of *Pfaffia paniculata, Ptychopetalum olacoides*, and *Lilium candidum* extracts; and (f) at least one humectant; (2) an emulsifier; and (3) a dermatologically acceptable carrier, wherein (a)-(f) are employed in amounts sufficient to synergistically neutralize existing free radicals present in the skin, while proactively priming the skin by repairing and/or protecting its *Stratum corneum* without unduly impairing the *Stratum corneum*'s acid mantle, in order to enhance the skin's ability to defend itself against free-radical aggression, thereby improving its health and appearance, and wherein the composition is natural, free of a skin-sensitizing amount of an essential oil, and has a pH ranging from about 4.5 to about 5.5, and preferably from about 4.8 to about 5.3.

According to another embodiment, the present disclosure is also directed to a composition intended for application onto human skin, the composition that includes (1) a preservative system; (2) a mixture of at least: (a) a leaf extract of *Aristotelia chilensis*; (b) a leaf extract of *Buddleja globosa*; and (c) a leaf extract of *Ugni molinae*; and (d) optionally, a bark/seed extract of *Entada phaseoloides*; (e) optionally, a blend of *Pfaffia paniculata, Ptychopetalum olacoides*, and *Lilium candidum* extracts; and (f) at least one humectant; (3) an emulsifier; and (4) a dermatologically acceptable carrier, wherein (a)-(f) are employed in amounts sufficient to synergistically neutralize existing free radicals present in the skin, while proactively priming the skin by repairing and/or protecting its *Stratum corneum* without unduly impairing the *Stratum corneum*'s acid mantle, in order to enhance the skin's ability to defend itself against free-radical aggression, thereby improving its health and appearance, and wherein the composition is natural, free of a skin-sensitizing amount of an essential oil, and has a pH ranging from about 4.5 to about 5.5, and preferably from about 4.8 to about 5.3.

The present disclosure is also directed to a method of treating and priming skin suffering from or at risk of suffering from oxidative stress in order to enhance its health and appearance by applying one of the above-disclosed compositions onto the skin.

According to another embodiment, the present disclosure is also directed to a method of proactively priming the skin by repairing and/or protecting its Stratum corneum without unduly impairing the Stratum corneum's acid mantle, in order to enhance the skin's ability to defend itself against free-radical aggression and dry skin-inducing water loss.

According to yet another embodiment, the present disclosure is directed to a natural preservative system that cooperates with a skin care composition and method for treating or addressing oxidative stress. The preservative system may be a preservative system as disclosed and/or claimed in U.S. Pat. No. 10,721,937, which issued on Jul. 28, 2020 and which enjoys a priority date of May 9, 2019. This patent is incorporated herein by reference in its entirety.

According to yet another embodiment, the present disclosure is directed to a skin care composition intended for application to the skin as a sun block or sunscreen product.

These and other features, aspects, and advantages of the present disclosure will become evident to those skilled in the art from a reading of the present disclosure.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which.

DETAILED DESCRIPTION

Figure 1:
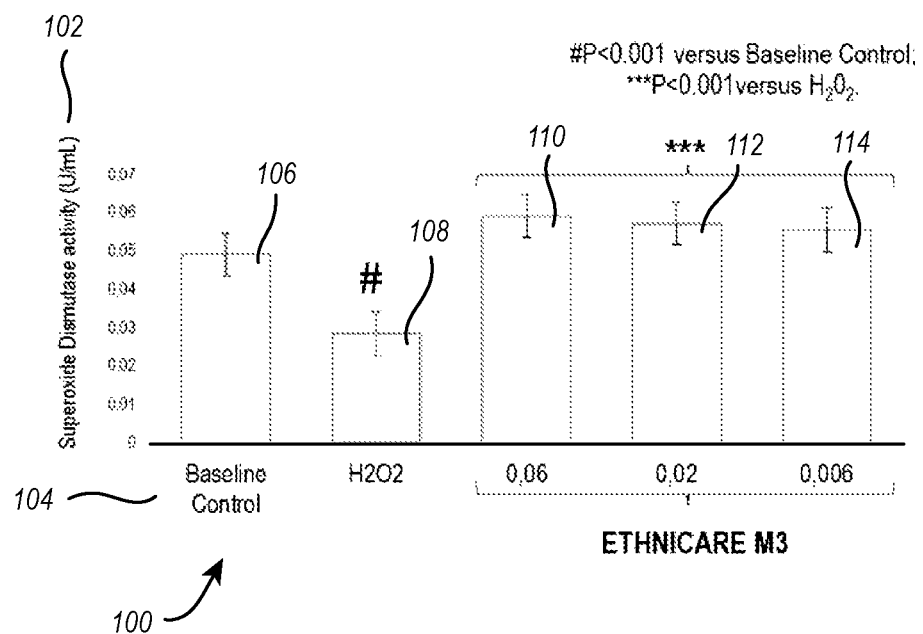
FIG. 1 illustrates levels of superoxide dismutase activity in response to different compositions including components of embodiments of the disclosure.

For purposes of the present disclosure, the use of the word "natural" is intended to encompass ECOCERT®-approved ingredients or formulations synonymous with the terms "green," "clean," "organic," "sustainable," "eco-friendly," or "environmentally-friendly" as known and used in the art. The term "natural," for example, may be used in the context of holistic or homeopathic formulations and is intended to include those topical consumer products and/or preservative systems that are plant-based, paraben-free, and/or non-toxic.

Further, when used in the context of the antimicrobial properties of a preservative or preservative system, the term "broad spectrum" is intended to describe those preservatives or preservative systems of the present disclosure that have the ability to inhibit the growth of or kill a wide range of microorganisms that decay or spoil topical consumer products. For example, a "broad spectrum" preservative system inhibits the growth of or kills a wide range of bacteria and fungi, preferably a wide range of Gram-positive and Gram-negative bacteria, yeasts, molds, and/or other fungi.

The compositions of the present disclosure can comprise, consist essentially of, or consist of, the components of the present disclosure as well as other ingredients described herein. The term "comprising" as used herein is meant to include various optional, compatible components that can be used in the preservative systems and cosmetic compositions of the present disclosure without limiting the inclusion, use of, or cooperation with other ingredients, excipients, uses, or otherwise. The term "consisting essentially of" as used herein means that the composition or component may include additional ingredients, but only if the additional ingredients do not materially alter the basic and novel characteristics of the compositions or methods.

As used herein, the words "preferred," "preferably," and variants thereof refer to embodiments of the disclosure that afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the disclosure.

Numerical ranges as used herein are intended to include every number and subset of numbers contained within that range, whether specifically disclosed or not. Further, these numerical ranges should be construed as providing support for a claim directed to any number or subset of numbers within that range.

All percentages, parts, proportions, and ratios as used herein are by weight of the total composition, unless otherwise specified. All such weights as they pertain to listed ingredients are based on the active level.

All references to singular characteristics or limitations of the present disclosure shall include the corresponding plural characteristic or limitation, and vice versa, unless otherwise specified or clearly implied to the contrary by the context in which the reference is made.

All publications, articles, papers, patents, patent publications, and other references cited herein are hereby incorporated in their entireties for all purposes to the extent consistent with the disclosure herein.

The terms "prime" and "priming" as described herein refer to the process of repairing and/or protecting the Stratum corneum without unduly impairing its acid mantle, in order to protect it from oxidative stress and dry skin-inducing water loss. One exemplary way that the acid mantle could be considered unduly impaired is by observing a reduced diversity or unnatural selection of microbes comprising the skin microbiome. This may correlate with a skin pH outside of normal homeostatic bounds.

The term "dry skin-inducing water loss" as described herein refers to an amount of trans-epidermal water loss (TEWL) that causes skin to become dry, flaky, itchy and/or irritated—symptomatic of an improperly functioning *Stratum corneum*/skin barrier.

The term "oxidative stress" as described herein refers to the disturbance in balance between reactive oxygen species (ROS) and/or free radicals and antioxidants present in the skin caused by extrinsic and/or intrinsic factors. Extrinsic factors include, for example, exposure to UV radiation, pollution, and products containing harsh chemicals. Intrinsic factors include, for example, chronological aging, a person's genetic makeup, and other biological changes that occur from within the skin.

The term "skin-sensitizing effective amount" as described herein is meant to exclude an amount of a volatile essential oil that can lead to an allergic response following contact with an individual's skin. Skin sensitization is an immunological response to previous exposure to a substance that results in an inflammatory skin reaction. An allergic skin reaction is usually presented as a red, itchy, bumpy rash. Examples of the types of volatile essential oils that can cause skin sensitization, depending on their amounts within a skin care composition include, but are not limited to, frankincense, myrrh, and sweet orange.

The term "free radicals" as described herein refers to those ROS that are formed when skin experiences oxidative stress caused by extrinsic factors including exposure to UV radiation and environmental stressors such as pollution and harmful chemical agents typically found, for example, in hard-surface cleaning products.

The present disclosure generally relates to compositions and methods for effectively alleviating oxidative stress in order to enhance human skin's health and appearance, while at the same time or alternatively enabling the skin to defend itself against further free-radical aggression and dry skin-inducing water loss by repairing and/or protecting the *Stratum corneum*/skin barrier in a way that does not unduly impair its acid mantle. Moreover, the composition is also natural, organic, and ECOCERT®-approved, thus being free of synthetic and/or petroleum-derived ingredients.

It has surprisingly been discovered by the inventors that a composition that is both natural and free of a skin sensitizing-effective amount of an essential oil, comprising a mixture of specific botanical infusions comprising at least: (a) a leaf extract of *Aristotelia chilensis*; (b) a leaf extract of *Buddleja globosa*; (c) a leaf extract of *Ugni molinae*; (d) optionally, a bark/seed extract of *Entada phaseoloides*; (e) optionally, a blend of *Pfaffia paniculata, Ptychopetalum olacoides*, and *Lilium candidum* extracts; and (f) at least one humectant, when applied onto skin, synergistically alleviates oxidative stress in order to enhance the skin's health and appearance, while at the same time priming the skin by repairing and/or protecting the *Stratum corneum* without unduly impairing it's acid mantle, in order to enable the skin to protect itself against future free radical aggression and dry skin-inducing water loss.

*Aristotelia chilensis* leaf extract is derived from the leaves of a small dioecious evergreen tree in the Elaeocarpaceae family native to South America in the Valdivian temperate rainforests of Chile, which also goes by the name maqui. The extract has been found to contain high amounts of anthocyanins, indole alkaloids, and flavonoids. These compounds serve as a source of antioxidants that help to neutralize free radicals and protect the skin's DNA.

This extract has also been found to be rich in the anthocyanidin delphinidin. In a study entitled "NADPH oxidase is a novel target of delphinidin for the inhibition of UVB-induced MMP-1 expression in human dermal fibroblasts," Lim T G, Jung S K, Kim Y, Lee H J, Tang T S, Lee K W, John Wiley & Sons Ltd, *Experimental Dermatology*, 2013, 22, 417-437, it was reported that delphinidin was effective at inhibiting UVB-induced MMP-1 expression in the skin, which is known to cause degradation of dermal collagen. Various enzyme systems in the skin are associated with endogenous ROS production, including the enzyme system NADPH oxidase (NOX), which plays a key role in triggering ROS production. Studies have shown that NOX activation is thus closely related to ROS-induced skin aging. The study concluded that delphinidin significantly inhibits UVB-induced MMP-1 expression in human dermal fibroblasts, which then inhibits NOX enzyme activation, which in turn inhibits ROS production, and therefore this particular anthocyanidin might prevent photoaging.

This extract is commercially available from N-Active EIRL under the trade name EthniCare® MAQUI.

The *Aristotelia chilensis* leaf extract is preferably employed in an amount of from about 1 to about 10% by weight, and most preferably from about 2 to about 5% by weight, based on the total weight of the composition.

*Buddleja globosa* leaf extract is derived from the leaves of the orange ball buddleja, a.k.a. matico, a species of flowering plant endemic to Chile and Argentina. The extract has been found to contain glycosidic flavonoids and phenylethanoids such as verbascoside, iridoids, triterpenoids, and di- and sesquiterpenoids, together with two caffeic acid derivatives. These compounds have shown promise in wound healing due to their ability to promote fibroblast growth, with a strong antioxidant effect. This particular leaf extract is also rich in stigmasterol, an unsaturated plant sterol found in plant oils.

In an article entitled "Analgesic, anti-inflammatory, and antioxidant properties of *Buddleja globosa*, Buddlejaceae," Backhouse N, Rosales L, Apablaza C, Goïty L, Erazo S, Negrete R, Theoduloz C, Rodriguez J, Delporte C J, *Ethnopharmacol*. 2008 Mar. 5; 116(2):263-9, it was reported that plant extracts having fractions rich in stigmasterol and β-sitosterol display anti-inflammatory properties. This extract is commercially available from N-Active EIRL, under the trade name EthniCare® MATICO.

The *Buddleja globosa* leaf extract is preferably employed in an amount of from about 0.5 to about 3% by weight, and most preferably from about 1 to about 2% by weight, based on the total weight of the composition.

*Ugni molinae* leaf extract is derived from the leaves of a woody evergreen shrub from the *myrtaceae* family commonly found in Chile and is also known by its Spanish name murta. The extract has been found to contain various phenolic compounds including gallic acid, catechin, quercetin, myricetin, and kaempferol. These compounds have been found to possess strong antioxidant activity against ROS production, lipid peroxidation, and superoxide anion production.

In an article entitled "MURTA (*Ugni molinae* Turcz.): A REVIEW ON CHEMICAL COMPOSITION, FUNCTIONAL COMPONENTS AND BIOLOGICAL ACTIVITIES OF LEAVES AND FRUITS," Lopez J, Vega-Galvez A, Rodriguez A, Uribe E, Bilbao-Sainz C, Chilean *J. Agric. Anim. Sci., ex Agro-Ciencia* (2018) 34(1):1-14, the *Ugni molinae* leaf extract was found to have large amounts of flavonoids (anthocyanins, flavonols, flavanols), condensed and hydrolysable tannins, stilbenoids (resveratrol), and phenolic acids, which possess both antioxidant and antimicrobial activity. As was mentioned previously, anthocyanins have been found to possess antioxidant/free radical scavenging properties that prevent oxidative stress, a phenomenon shown to negatively affect skin health and appearance.

The *Ugni molinae* leaf extract is preferably employed in an amount of from about 0.5 to about 3% by weight, and most preferably from about 1 to about 2% by weight, based on the total weight of the composition. This extract is commercially available from N-Active EIRL, under the trade name EthniCare® MURTA.

*Entada phaseoloides* bark/seed extract is derived from the seeds of a woody, evergreen vine from the *Fabaceae* family found in Africa, Asia, Australia, and the western Pacific. Its primary molecules include Entadamide A and Phaseoloidin. Entadamide A limits urocanic acid isomerization in skin, thereby inhibiting inflammation and immunosuppression, while also serving as a UV absorber. Phaseoloidin, a homogentisic acid glucoside, is a molecule with superior free-radical scavenging ability.

In a study entitled, "Experimental evaluation of anti-inflammatory effect of topical application of *entada phaseoloides* seeds as paste and ointment," Dawane J, Pandit V, Rajopadhye B, N Am J Med Sci. 2011 November; 3(11): 513-517, the topical application of a paste and ointment containing the *Entada phaseoloides* bark/seed extract was confirmed as having potent anti-inflammatory properties.

The *Entada phaseoloides* bark/seed extract may be employed in an amount of from about 1 to about 5% by weight, and preferably in an amount of from about 2 to about 3% by weight, based on the total weight of the composition. This extract is commercially available from Biosil Technologies, Inc. headquartered in Allendale, N.J., under the trade name Entadine®.

The blend of the present disclosure comprises *Pfaffia paniculata, Ptychopetalum olacoides*, and *Lilium candidum* extracts. *Pfaffia paniculata* root extract is derived from a plant in the Amaranthaceae family typically found in South America. It is an extract characterized by the presence of vitamins, minerals, amino acids, phytosterols, pfaffic acid, pfaffosides, allantoin, mucilage, and saponins. This extract has been found to possess anti-inflammatory, immunostimulant, and analgesic properties.

*Ptychopetalum olacoides* bark/stem extract is derived from a flowering plant in the *Olacaceae* family indigenous to central Amazonian forests. The extract, which possesses antioxidant properties, is characterized by the presence of alkaloids, resinous materials rich in organic acids and tannins, traces of essential oils, sterols, triterpenic alcohols, and lupeol.

*Lilium candidum* extract is derived from the bulbs and flowers of the Liliaceae family. It is characterized by the presence of amino acids, flavonoids, glycosides, and steroids, and has been found to possess antifungal and anti-inflammatory properties. The blend of *Pfaffia paniculata, Ptychopetalum olacoides*, and *Lilium candidum* extracts is commercially available from Chemyunion LTDA, a Brazilian company headquartered in Sao Paulo, under the name Bioskinup™ Contour 3R.

The blend may be employed in embodiments of the disclosure in an amount of from about 1 to about 5% by weight, and preferably in an amount of from about 2 to about 3% by weight, based on the total weight of the composition.

The composition of the present disclosure further includes at least one humectant in order to further enhance the hydration and moisturization of the skin, thereby providing enhanced priming. The humectant will typically be employed in an amount of from about 1.0 to about 6.0% by weight, and preferably from about 1.5 to about 4.0% by weight, based on the total weight of the composition. Examples of suitable humectants include, but are not limited to, hyaluronic acid and its derivatives such as sodium hyaluronate and hydrolyzed hyaluronic acid, lecithin, aloe vera, panthenol, glycerin, and seaweed. A particularly preferred humectant for use in embodiments of the skin care compositions and methods of the present disclosure is hydrolyzed hyaluronic acid.

According to one embodiment of the present disclosure, there is provided a composition intended for application onto human skin suffering or at risk of suffering from oxidative stress, the composition comprising: (1) a mixture of at least: (a) from about 1 to about 10% by weight, and preferably from about 2% to about 5% by weight, of a leaf extract of *Aristotelia chilensis*; (b) from about 0.5 to about 3% by weight, and preferably from about 1 to about 2% by weight, of a leaf extract of *Buddleja globosa*; (c) from about 0.5 to about 3% by weight, and preferably from about 1 to about 2% by weight, of a leaf extract of *Ugni molinae*; (d) optionally, from about 1 to about 5% by weight, and preferably from about 2 to about 3% by weight, of a bark/seed extract of *Entada phaseoloides*; (e) optionally, from about 1 to about 5% by weight, and preferably from about 2 to about 3% by weight, of a blend of *Pfaffia paniculata, Ptychopetalum olacoides*, and *Lilium candidum* extracts; and (f) from about 1 to about 8% by weight, and preferably from about 2 to about 6% by weight, of at least one humectant, all weights based on the total weight of the composition; (2) an emulsifier; and (3) a dermatologically acceptable carrier, wherein (a)-(f) are employed in amounts sufficient to neutralize existing free radicals present in the skin, while proactively priming the skin by repairing and/or protecting its *Stratum corneum* without unduly impairing the *Stratum corneum*'s acid mantle, in order to enhance the skin's ability to defend itself against free-radical aggression, thereby improving its health and appearance, and wherein the composition is natural, free of a skin-sensitizing amount of an essential oil, and has a pH ranging from about 4.5 to about 5.5, and preferably from about 4.8 to about 5.3.

In another embodiment of the present disclosure, the inventors have surprisingly discovered that a natural preservative system comprising a combination of specific amounts of: a *Lactobacillus* ferment, a *Lactobacillus* and *Cocos nucifera* (coconut) fruit extract, salicylic acid (in some embodiments optional), a salt of a weak acid such as potassium sorbate, and propanediol which is optionally petroleum-free, when incorporated into a composition having a specific pH range, effectively both prohibits and inhibits microbial growth on and in the composition.

The *Lactobacillus* ferment of the present disclosure is preferably employed in an amount of from about 1 to about 5% by weight, preferably from about 2 to about 4% and more preferably from about 2 to about 4%, by weight of the total composition. A "*Lactobacillus* ferment" may refer to the solution obtained after fermentation of a defined growth medium by the bacterium *Lactobacillus* spp. During fermentation, *Lactobacillus* bacteria produce antimicrobial peptides that can provide broad spectrum antimicrobial protection at appropriate concentrations and/or in combination with other antimicrobial agents. An exemplary *Lactobacillus* ferment is commercially available from Active Micro Technologies under the tradename Leucidal® SF.

The *Lactobacillus* and *Cocos nucifera* fruit extract can include any *Cocos nucifera* fruit extract fermented with *Lactobacillus* and/or included with *Lactobacillus* ferment of the present disclosure and is preferably employed in an amount of from about 1 to about 5%, preferably from about 2 to about 4%, by weight of the total composition. "*Cocos nucifera* fruit extract fermented with *Lactobacillus*," may reference the solution obtained after *Lactobacillus* fermentation of *Cocos nucifera* (coconut) fruit extract instead of a defined growth medium. The result is a materially different antimicrobial product that is effective at preventing the growth of fungi, specifically yeasts and molds, at appropriate concentrations and/or in combination with other antimicrobial agents. An exemplary *Lactobacillus* and *Cocos nucifera* extract is commercially available from Active Micro Technologies under the tradename Amticide® Coconut and is typically associated with the International Nomenclature of Cosmetic Ingredients (INCI) name of a *Lactobacillus* and *Cocos nucifera* (coconut) fruit extract.

When present, salicylic acid is preferably employed in an amount of up to about 0.5% by weight, preferably from about 0.1 to about 0.45% and more preferably from about 0.2 to about 0.4%, by weight of the total composition. It should be noted that the use of salicylic acid in an amount at or greater than about 0.5% by weight, based on the total weight of the composition, renders the composition a drug requiring FDA approval prior to commercialization and sale in the United States. In some embodiments, salicylic acid may be omitted by adjusting the concentrations of *Lactobacillus* ferment, *Lactobacillus* and *Cocos nucifera* fruit extract, and/or other ingredients as described in greater detail herein.

The salt of a weak acid is preferably employed in an amount of up to about 0.5% by weight, preferably from about 0.1 to about 0.45% and more preferably from about 0.2% to about 0.4%, by weight of the total composition. A preferred salt of a weak acid is potassium sorbate (i.e., the potassium salt of sorbic acid). Other weak acids that may be used in their salt form include, but are not limited to, acetic acid, propionic acid, and benzoic acid.

Propanediol, such as a petroleum-free 1,3-propanediol, is typically employed in an amount of about 1% to about 10% by weight, preferably from about 2% to about 8% and more preferably from about 4% to about 6%, by weight of the total composition. An exemplary petroleum-free 1,3-propanediol is commercially available from Dupont Tate & Lyle Bio Products under the tradename Zemea® Propanediol and can be associated with the INCI name propanediol.

The inventors have unexpectedly discovered that the ability of the preservative system of the present disclosure to effectively inhibit microorganism growth is critically dependent on the pH of the composition in which it is used. For example, if the preservative system is employed in a composition having a pH of 6, it fails to provide the requisite broad-spectrum protection needed for acceptable storage stability/shelf-life. Accordingly, the pH of a composition comprising the preservative system of the present disclosure may be in a range of from about 4.5 to about 5.5, and preferably from about 4.8 to about 5.3.

According to this embodiment of the present disclosure, there is provided a composition intended for application onto human skin in order to enhance its health and appearance, the composition comprising: (1) a preservative system that includes: (a) from about 1 to about 5%, preferably from about 2 to about 4% by weight, of a *Lactobacillus* ferment; (b) from about 1 to about 5%, preferably from about 2 to about 4% by weight, of a *Lactobacillus* and *Cocos nucifera* fruit extract; (c) up to about 0.5% by weight, preferably from about 0.1 to about 0.45, and most preferably from about 0.25 to about 0.4% by weight of salicylic acid; (d) from about 0.1 to about 0.5% by weight, and preferably from about 0.2 to about 0.4% by weight of at least one salt of a weak acid, preferably potassium sorbate; and (e) from about 1 to about 10%, preferably from about 2 to about 8% by weight, and most preferably from about 4 to about 6% by weight of 1,3-propanediol; (2) a mixture of at least: (f) from about 1 to about 10% by weight, and preferably from about 2 to about 5% by weight, of a leaf extract of *Aristotelia chilensis*; (g) from about 0.5 to about 3% by weight, and preferably from about 1 to about 2% by weight, of a leaf extract of *Buddleja globosa*; (h) from about 0.5 to about 3% by weight, and preferably from about 1 to about 2% by weight, of a leaf extract of *Ugni molinae*; (i) optionally, from about 1 to about 5% by weight, and preferably from about 2 to about 3% by weight, of a bark/seed extract of *Entada phaseoloides*; (j) optionally, from about 1 to about 5% by weight, and preferably from about 2 to about 3% by weight, of a blend of *Pfaffia paniculata, Ptychopetalum olacoides*, and *Lilium candidum* extracts; and (k) from about 1 to about 8% by weight, and preferably from about 2 to about 6% by weight, of at least one humectant, all weights based on the total weight of the composition; (3) an emulsifier; and (4) a dermatologically acceptable carrier, wherein (f)-(k) are employed in amounts sufficient to neutralize existing free radicals present in the skin, while proactively priming the skin by repairing and/or protecting its *Stratum corneum* without unduly impairing the *Stratum corneum*'s acid mantle, in order to enhance the skin's ability to defend itself against free-radical aggression, thereby improving its health and appearance, and wherein the composition is natural, free of a skin-sensitizing amount of an essential oil, and has a pH ranging from about 4.5 to about 5.5, and preferably from about 4.8 to about 5.3.

In another embodiment of the present disclosure, there is provided a composition intended for application onto human skin in order to enhance its health and appearance, the composition comprising: (1) a preservative system that includes: (a) from about 1 to about 5%, preferably from about 2 to about 4% by weight, of a *Lactobacillus* ferment; (b) from about 1 to about 5%, preferably from about 2 to about 4% by weight of a *Cocos nucifera* fruit extract fermented with *Lactobacillus*; (c) from about 0.1 to about 0.45% by weight, preferably from about 0.25 to about 0.4% of salicylic acid; (d) up to about 0.5% by weight, preferably from about 0.2 to about 0.4% by weight, of at least one salt of a weak acid, preferably potassium sorbate; and (e) from about 1 to about 10%, preferably from about 2 to about 8% by weight, and most preferably from about 4 to about 6% by weight, of a petroleum-free propanediol; (2) a mixture of at least: (f) from about 1 to about 10% by weight, and preferably from about 2 to about 5% by weight, of a leaf extract of *Aristotelia chilensis*; (g) from about 0.5 to about 3% by weight, and preferably from about 1 to about 2% by weight, of a leaf extract of *Buddleja globosa*; (h) from about 0.5 to about 3% by weight, and preferably from about 1 to about 2% by weight, of a leaf extract of *Ugni molinae*; (i) optionally, from about 1 to about 5% by weight, and preferably from about 2 to about 3% by weight, of a bark/seed extract of *Entada phaseoloides*; (j) optionally, from about 1 to about 5% by weight, and preferably from about 2 to about 3% by weight, of a blend of *Pfaffia paniculata, Ptychopetalum olacoides*, and *Lilium candidum* extracts; and (k) from about 1 to about 8% by weight, and preferably from about 2 to about 6% by weight, of at least one humectant, all weights based on the total weight of the composition; (3) an emulsifier; and (4) a dermatologically acceptable carrier, wherein (f)-(k) are employed in amounts sufficient to neutralize existing free radicals present in the skin, while proactively priming the skin by repairing and/or protecting its *Stratum corneum* without unduly impairing the *Stratum corneum*'s acid mantle, in order to enhance the skin's ability to defend itself against free-radical aggression, thereby improving its health and appearance, and wherein the composition is natural, free of a skin-sensitizing amount of an essential oil, and has a pH ranging from about 4.5 to about 5.5, and preferably from about 4.8 to about 5.3.

According to yet another embodiment of the present disclosure, there is provided a composition intended for application onto human skin in order to enhance its health and appearance, the composition comprising: (1) a preservative system that includes: (a) from about 1 to about 5%, preferably from about 2 to about 4% by weight, of a *Lactobacillus* ferment; (b) from about 1 to about 5%, preferably from about 2 to about 4% by weight, of a *Cocos nucifera* fruit extract fermented with *Lactobacillus*; (c) from about 0.1 to about 0.45%, preferably from about 0.25 to about 0.4% by weight, of salicylic acid; (d) from about 0.1 to about 0.5% by weight, preferably from about 0.2 to about 0.4% by weight, of at least one salt of a weak acid, preferably potassium sorbate; and (e) from about 1 to about 10%, preferably from about 2 to about 8%, and most preferably from about 4 to about 6% by weight, of a petroleum-free 1,3-propanediol; (2) a mixture of at least: (f) from about 1 to about 10% by weight, and preferably from about 2 to about 5% by weight, of a leaf extract of *Aristotelia chilensis*; (g) from about 0.5 to about 3% by weight, and preferably from about 1 to about 2% by weight, of a leaf extract of *Buddleja globosa*; (h) from about 0.5 to about 3% by weight, and preferably from about 1 to about 2% by weight, of a leaf extract of *Ugni molinae*; (i) optionally, from about 1 to about 5% by weight, and preferably from about 2 to about 3% by weight, of a bark/seed extract of *Entada phaseoloides*; (j) optionally, from about 1 to about 5% by weight, and preferably from about 2 to about 3% by weight, of a blend of *Pfaffia paniculata, Ptychopetalum olacoides*, and *Lilium candidum* extracts; and (k) from about 1 to about 8% by weight, and preferably from about 2 to about 6% by weight, of at least one humectant, all weights based on the total weight of the composition; (3) an emulsifier; and (4) a dermatologically acceptable carrier, wherein (f)-(k) are employed in amounts sufficient to neutralize existing free radicals present in the skin, while proactively priming the skin by repairing and/or protecting its *Stratum corneum* without unduly impairing the *Stratum corneum*'s acid mantle, in order to enhance the skin's ability to defend itself against free-radical aggression, thereby improving its health and appearance, and wherein the composition is natural, free of a skin-sensitizing amount of an essential oil, and has a pH ranging from about 4.5 to about 5.5, and preferably from about 4.8 to about 5.3.

In yet another embodiment of the present disclosure, there is provided a composition intended for application onto human skin in order to enhance its health and appearance, the composition comprising: (1) a preservative system comprised of: (a) from about 2 to about 4% by weight, of a *Lactobacillus* ferment; (b) from about 2 to about 4% by weight, of a *Cocos nucifera* fruit extract fermented with *Lactobacillus*; (c) from about 0.25 to about 0.4% by weight, of salicylic acid; (d) from about 0.2 to about 0.4% by weight, of at least one salt of a weak acid, preferably potassium sorbate; and (e) from about 4 to about 6% by weight, of a petroleum-free 1,3-propanediol; (2) a mixture of at least: (f) from about 1 to about 10% by weight, and preferably from about 2 to about 5% by weight, of a leaf extract of *Aristotelia chilensis*; (g) from about 0.5 to about 3% by weight, and preferably from about 1 to about 2% by weight, of a leaf extract of *Buddleja globosa*; (h) from about 0.5 to about 3% by weight, and preferably from about 1 to about 2% by weight, of a leaf extract of *Ugni molinae*; (i) optionally, from about 1 to about 5% by weight, and preferably from about 2 to about 3% by weight, of a bark/seed extract of *Entada phaseoloides*; (j) optionally, from about 1 to about 5% by weight, and preferably from about 2 to about 3% by weight, of a blend of *Pfaffia paniculata, Ptychopetalum olacoides*, and *Lilium candidum* extracts; and (k) from about 1 to about 8% by weight, and preferably from about 2 to about 6% by weight, of at least one humectant, all weights based on the total weight of the composition; (3) an emulsifier; and (4) a dermatologically acceptable carrier, wherein (f)-(k) are employed in amounts sufficient to neutralize existing free radicals present in the skin, while proactively priming the skin by repairing and/or protecting its *Stratum corneum* without unduly impairing the *Stratum corneum*'s acid mantle, in order to enhance the skin's ability to defend itself against free-radical aggression, thereby improving its health and appearance, and wherein the composition is natural, free of a skin-sensitizing amount of an essential oil, and has a pH ranging from about 4.5 to about 5.5, and preferably from about 4.8 to about 5.3.

According to another embodiment of the present disclosure, there is provided a composition intended for application onto human skin in order to enhance its health and appearance, the composition comprising: (1) a preservative system comprised of: (a) from about 2 to about 4% by weight, of a *Lactobacillus* ferment; (b) from about 2 to about 4% by weight, of a *Cocos nucifera* fruit extract fermented with *Lactobacillus*; (c) from about 0.25 to about 0.4% by weight, of salicylic acid; (d) from about 0.2 to about 0.4% by weight, of at least one salt of a weak acid, preferably potassium sorbate; and (e) from about 4 to about 6% by weight, of a petroleum-free 1,3-propanediol; (2) a mixture of at least: (f) from about 1 to about 10% by weight, and preferably from about 2 to about 5% by weight, of a leaf extract of *Aristotelia chilensis*; (g) from about 0.5 to about 3% by weight, and preferably from about 1 to about 2% by weight, of a leaf extract of *Buddleja globosa*; (h) from about 0.5 to about 3% by weight, and preferably from about 1 to about 2% by weight, of a leaf extract of *Ugni molinae*; (i) optionally, from about 1 to about 5% by weight, and preferably from about 2 to about 3% by weight, of a bark/seed extract of *Entada phaseoloides*; (j) optionally, from about 1 to about 5% by weight, and preferably from about 2 to about 3% by weight, of a blend of *Pfaffia paniculata, Ptychopetalum olacoides*, and *Lilium candidum* extracts; and (k) from about 1 to about 8% by weight, and preferably from about 2 to about 6% by weight, of at least one humectant, all weights based on the total weight of the composition; (3) an emulsifier; and (4) a dermatologically acceptable carrier, wherein (f)-(k) are employed in amounts sufficient to neutralize existing free radicals present in the skin, while proactively priming the skin by repairing and/or protecting its *Stratum corneum* without unduly impairing the *Stratum corneum*'s acid mantle, in order to enhance the skin's ability to defend itself against free-radical aggression, thereby improving its health and appearance, and wherein the composition is natural, free of a skin-sensitizing amount of an essential oil, and has a pH ranging from about 4.5 to about 5.5, and preferably from about 4.8 to about 5.3.

According to another embodiment of the present disclosure, there is provided a composition intended for application onto human skin in order to enhance its health and appearance, the composition comprising: (1) a preservative system comprised of: (a) about 4% by weight, of a *Lacto-* bacillus ferment; (b) about 4% by weight, of a *Cocos nucifera* fruit extract fermented with *Lactobacillus*; (c) about 0.4% by weight, of potassium sorbate; and (e) about 4% by weight, of a petroleum-free 1,3-propanediol; (2) a mixture of at least: (f) from about 1 to about 10% by weight, and preferably from about 2 to about 5% by weight, of a leaf extract of *Aristotelia chilensis*; (g) from about 0.5 to about 3% by weight, and preferably from about 1 to about 2% by weight, of a leaf extract of *Buddleja globosa*; (h) from about 0.5 to about 3% by weight, and preferably from about 1 to about 2% by weight, of a leaf extract of *Ugni molinae*; (i) optionally, from about 1 to about 5% by weight, and preferably from about 2 to about 3% by weight, of a bark/seed extract of *Entada phaseoloides*; (j) optionally, from about 1 to about 5% by weight, and preferably from about 2 to about 3% by weight, of a blend of *Pfaffia paniculata, Ptychopetalum olacoides*, and *Lilium candidum* extracts; (k) from about 1 to about 8% by weight, and preferably from about 2 to about 6% by weight, of at least one humectant, all weights based on the total weight of the composition; (3) an emulsifier; and (4) a dermatologically acceptable carrier, wherein (f)-(j) are employed in amounts sufficient to neutralize existing free radicals present in the skin, while proactively priming the skin by repairing and/or protecting its Stratum corneum without unduly impairing the Stratum corneum's acid mantle, in order to enhance the skin's ability to defend itself against free-radical aggression, thereby improving its health and appearance, and wherein the composition is natural, free of a skin-sensitizing amount of an essential oil, and has a pH ranging from about 4.5 to about 5.5, and preferably from about 4.8 to about 5.3.

The dermatologically acceptable carrier can encompass a wide variety of forms. In some cases, the solubility or dispersibility of the components in the composition may dictate the form and character of the carrier. Non-limiting examples include simple solutions (e.g., aqueous or anhydrous), dispersions, emulsions, and solid forms. In certain embodiments, the dermatologically acceptable carrier is in the form of an emulsion. An emulsion can be generally classified as having a continuous aqueous phase (e.g., oil-in-water and water-in-oil-in-water) or a continuous oil phase (e.g., water-in-oil or oil-in-water). While the oil phase may comprise any vegetable oil, so long as it does not cause skin sensitization, a particularly preferred oil component is almond oil.

The inventors have surprisingly discovered that the use of almond oil enables compounds present in the botanical extract to effectively penetrate into the skin, without having to use skin-sensitizing essential oils, while still facilitating the desired degree of efficacy. This is due to almond oil being rich in beta-zoosterol, squalene, and alpha-tocopherol, together with lesser amounts of carbohydrates, proteins, vitamins, and minerals such as vitamin B complex (comprising vitamins B1, B2, B3, B5, B6, B7, B9, B12) and zinc. Moreover, almond oil's phytochemicals are believed to be effective at inducing surface level proliferation and skin cell development. Other oils that may also be used include, but are not limited to, vegetable oils such as olive oil, jojoba oil, babassu oil, castor oil, coconut oil, corn oil, cotton seed oil, linseed oil, mustard oil, safflower oil, sesame oil, soybean oil, sunflower seed oil, wheat germ oil, argan oil and manila oil.

Any ingredient capable of emulsifying the composition may be employed as an emulsifier without departing from the spirit of the disclosure, so long as it is natural and/or dermatologically acceptable. Examples thereof include, but are not limited to, glyceryl stearate, cetyl alcohol, sodium stearoyl lactylate, sorbitan olivate, cetearyl olivate, cetearyl alcohol, cetearyl glucoside, sodium cetearyl sulfate, and the like. It is also particularly preferred that the emulsifier be free of palm oil.

The compositions of the present disclosure may be made available to consumers in a wide variety of product forms that include, but are not limited to, solutions, suspensions, lotions, creams, gels, sprays, ointments, foams, and serums. For example, a product intended for application onto skin, post-shaving, in order to help relieve the irritation associated with the mechanical stress on the skin caused by the shaving process, can be formulated using the above-described compositions as a base formula.

In an embodiment, a product intended for application onto skin prior to or during exposure to sunlight, in order to serve as a sunscreen or sun block, may be formulated according to the above-described compositions as a base formula.

According to embodiments of the present disclosure, the compositions can also additionally comprise suitable optional ingredients as desired. For example, the composition can optionally include other active or inactive ingredients, provided they do not unacceptably alter the benefits of the skin care composition, are natural, and/or do not promote skin sensitization. The precise amount of optional ingredients will be determined by those skilled in the art.

Examples of optional additive ingredients that may be employed include, but are not limited to, humectants, emollients, flavonoids, minerals, chelating agents, pH regulators/buffers, rheology modifiers, phytosterols, vitamin B3 compound, anti-inflammatory agents such as licorice extracts, bisabolol, manjistha extracted from plants in the genus *Rubia*, guggal extracted from plants in the genus *Commiphora, Quillaja saponaria* extract, kola extract, chamomile, red clover extract, sea whip extract, hibiscus extract, lucuma extract, ficus extract, red algae extract, sea kale extract, Iceland Moss extract, Saskatoon Berry extract, Siberian Ginseng extract, spruce needles extract, birch bark extract, yarrow extract, marigold extract, and couch grass extract.

Additional ingredients that may be employed in order to further potentiate the disclosure's efficacy may include, for example, *Peumus boldus* (Boldo) leaf extract, *Astrocaryum murumuru* seed butter, *Butyrospermum parkii* (shea) butter, *Theobroma grandiflorum* seed butter, *Spondias mombin* pulp extract, *Mangifera indica* pulp extract, *Musa sapientum* pulp extract, *Mauritia flexuosa* fruit oil, *Physalis angulata* extract, *Xylityl sesquicaprylate, Vaccinium myrtillus* seed oil, *Cucubita pepo* seed extract, linoleic acid, linolenic acid, *Centella asiatica* leaf extract, *Tamarindus indica* seed polysaccharide, *Zanthoxylum bungeanum* fruit extract, *Lactococcus* ferment lysate, *Bellis perennis* flower extract, *Coffea arabica* seed cake extract, *Coffea arabica* seed oil, cotton seed oil, linseed oil, *Pichia* ferment lysate filtrate, whey protein, mango, *mombin* plum and dragon's blood.

A particularly preferred optional ingredient for use in the composition of the present disclosure is an emollient which may be employed in an amount of from about 1 to about 15% by weight, preferably from about 2 to about 5% by weight, and all weights therebetween. Examples of preferred emollients include, but are not limited to, seed butters such as *Astrocaryum murumuru* seed butter and *Theobroma grandiflorum* seed butter. These seed butters provide an enhanced degree of emollience to the compositions of the present disclosure. An especially preferred seed butter is *Astrocaryum murumuru* seed butter.

In addition to the above-mentioned ingredients, certain types of auxiliary ingredients may also be added to the composition of the present disclosure in order to prophylactically inhibit free-radical formation caused by UV radiation, which induces oxidative stress in the skin, in order to facilitate photoinhibition.

Examples of such auxiliary ingredients include, but are not limited to, *pongamia glabra* (karanja) seed oil derived from the pongolote tree, *Dunaliella salina* algae extract which is rich in beta-carotene, *Haematococcus pluvialis* algae extract which is rich in astaxanthin, red algae which is rich in mycosporine-like amino acids, zinc oxide, and titanium dioxide.

The *Peumus boldus* (Boldo) leaf extract, when employed, will typically be used in an amount of from about 0.1 to about 5.0% by weight, such as from about 0.5 to about 3.0% by weight, and from about 1.0 to about 2.0% by weight, based on the weight of the composition.

In yet another embodiment of the present disclosure, there is provided a method of treating and/or priming skin suffering from oxidative stress or at risk of suffering from oxidative stress in order to enhance its health and/or appearance, by applying one of the above-disclosed compositions onto the skin.

A further embodiment of the present disclosure provides for a method of proactively priming and enhancing human skin's ability to defend itself against future free radical aggression by applying one of the above-disclosed compositions onto the skin.

EXAMPLES

The following examples as set forth herein are intended for illustrative purposes only and are not intended to limit the scope of the disclosure in any way, as many variations thereof are possible without departing from the spirit and scope of the disclosure. In the examples, all concentrations are listed as weight percent, unless otherwise specified.

Example 1

A mixture of: *Aristotelia chilensis*+*Buddleja globosa*+*Ugni molinae* leaf extracts (hereinafter, "EthniCare® M3") was evaluated for total glutathione quantification and superoxide dismutase (SOD) activity, in a lysate cell via an enzymatic assay. The absorbance reading was performed at 410 nm for total glutathione and 450 nm for SOD using a Multiscan GO monochromator available from Thermo Fisher Scientific of Waltham, Mass. The quantification values were normalized by the total protein in the sample using the Bradford technique, as described in *Anal. Biochem*, 72:248-254.

Primary human fibroblasts were seeded in 75 cm² flasks, cultured, and expanded in an incubator at 37° C. in the presence of 5% $CO_2$. Upon reaching confluency, the cells were seeded in well plates and exposed to hydrogen peroxide and the quantification mediators.

For statistical evaluation, an ANOVA test was used to initially measure the variation in the results, after which a Bonferroni post-test was used to make the ANOVA results even more precise. A 5% significance level was used.

The bar graph 100 of FIG. 1 shows the amount of SOD activity in human fibroblasts exposed to varying amounts of EthniCare® M3 110, 112, 114, as compared to the oxidative stress group $H_2O_2$ 108 and a baseline control 106 ($P<0.001$).

Here, it is seen that EthniCare® M3 110, 112, 114 resulted in a significant increase in protective effect against oxidative stress, at various concentration levels, based on increased SOD activity, with a standard deviation of 3. Hence, whereas oxidative stress caused by exposing the human fibroblasts to $H_2O_2$ 108 resulted in a decrease of SOD activity, subsequent exposure by EthniCare® M3 increased SOD activity by approximately 100%.

With regards to total glutathione production in human fibroblasts, the bar graph 200 in FIG. 2 below further corroborates the protective effect obtained when using EthniCare® M3.

Here too it is seen that EthniCare® M3 results in a significant increase in human fibroblast protective effect against oxidative stress, at various concentration levels 210, 212, 214 of EthniCare® M3, based on increased total glutathione production, with the same standard deviation of 3. Hence, whereas oxidative stress to human fibroblasts caused by $H_2O_2$ 208 exposure resulted in a decrease of total glutathione, subsequent exposure to EthniCare® M3 210, 212, 214 significantly increased total glutathione production.

Figure 2:
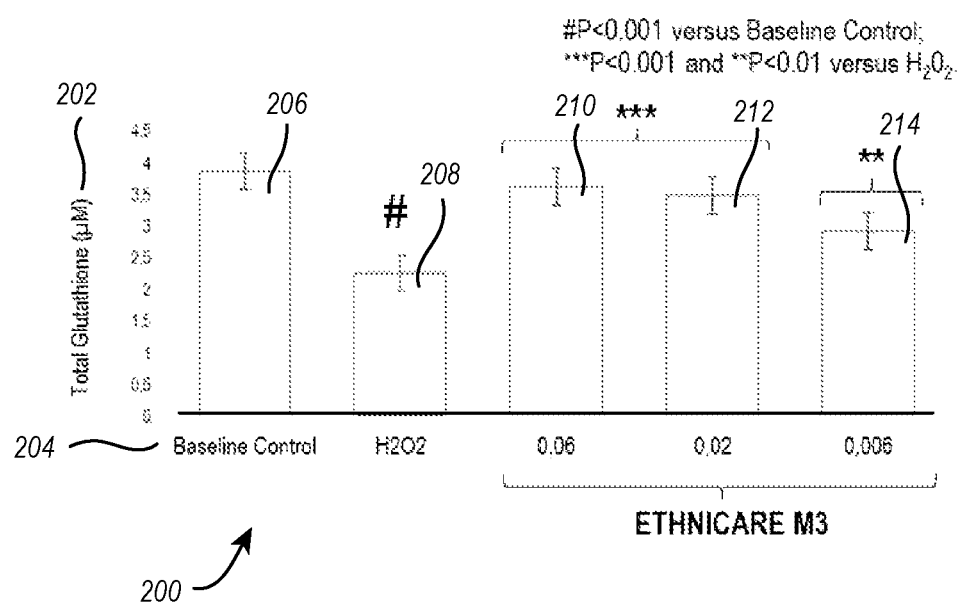
FIG. 2 illustrates levels of superoxide dismutase activity in response to different compositions including components of embodiments of the disclosure.

The results in FIGS. 1 and 2 demonstrate the significant antioxidant activity realized by EthniCare® M3, in view of its ability to strengthen cellular antioxidant capacity by modulating the antioxidant mediators SOD and total glutathione.

Example 2

In this example, the photo-protective effect of EthniCare® M3 against visible light ranging from 400-700 nm was evaluated, since long-term exposure to visible light has been shown to induce oxidative stress that can contribute to unwanted skin pigmentation (dark spots), inflammation, and oxidative photo-aging. Visible blue radiation (440-485 nm), also referred to as "blue light," has the ability to penetrate deeper into the skin than both UVA and UVB light, all the way to the dermis where collagen and elastin reside. Aside from the sun, electronic devices such as smart phones and computer screens emit blue light that most people are exposed to, in large quantities, on a daily basis. The potential negative photo-aging consequences such exposure can have on skin is troubling.

In order to assess its blocking ability, a thin film of EthniCare® M3 was applied onto a Helioplate HD6 substrate from HelioScreen Labs. Transmission spectra were then obtained using a UV 2450 Shimadzu spectrophotometer with an integration sphere (ISR-240A), available from Shimadzu Corporation of Kyoto, Japan. The spectral sweep range was 400-700 nm with measurements taken three times to ensure accuracy, the results of which are found in FIG. 3.

Figure 3:
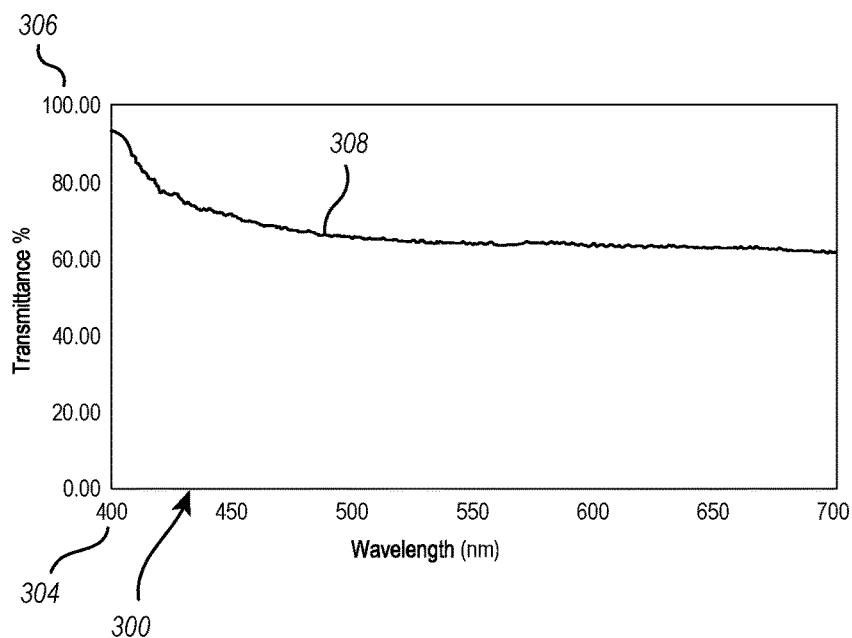
FIG. 3 illustrates transmissions spectra of components of embodiments of the disclosure.

As can be seen from the graph 300 of FIG. 3, the average transmittance 306 of blue light in the range of 440-485 nm, i.e. the UV range, is approximately 67%, with the mean being approximately 69%. Thus, approximately 31%, or one-third, of the blue light radiation was effectively blocked by EthniCare® M3, further evidencing its ability to inhibit oxidative stress and photo-aging damage.

Example 3

Leaf extracts *Aristotelia chilensis* and *Ugni molinae* were evaluated to determine their ability to prevent undesirable thymidine dimer formation upon exposure to UVB radiation. When skin is exposed to UVB radiation, thymidine bases in the DNA can absorb the UVB radiation to form thymidine dimers (also known as thymine dimers) in DNA, complicating the cell's efforts to replicate DNA and to properly function. In this experiment, an in-vitro thymidine dimer assay was performed using a skin model consisting of normal human-derived epidermal keratinocytes cultured to form a multilayered model of the human epidermis.

One group of tissue was treated for seven days with the *Aristotelia chilensis* leaf extract, another group of tissue was tested for seven days with the *Ugni molinae* leaf extract, and third group was left untreated. All three groups tissue groups were then exposed to UVB radiation at 300 mJ/cm$^2$. DNA was then extracted and assayed for thymidine dimer content.

The DNA was then immobilized and incubated with an antibody specific to thymidine dimers. The primary antibody was then detected with a secondary antibody conjugated to a fluorescent dye. The membrane was then scanned with an excitation laser and emission filter combo specific to the fluorescent dye, so that the fluorescence intensity of each sample was proportional to the amount of thymidine dimers present in the sample and a lower fluorescence intensity advantageously indicates lower levels of cellular damage from UVB radiation. The results of the thymidine dimer assay are found in Table 1, below, expressed as mean Relative Fluorescence Units (RFU)±standard deviation.

TABLE 1

|  | Corrected RFU |
| --- | --- |
| No UVB exposure | 514 ± 57.30 |
| Untreated | 5.463 ± 80.50 |
| 50 ug/ml Trolox (analog of vitamin E) | 4.380 ± 393.00 |
| *Aristotelia chilensis* at 5% | 3.418 ± 673.10 |
| *Ugni molinae* at 4% | 4.246 ± 426.30 |

The data in Table 1 shows that tissue treated with *Aristotelia chilensis* at 5% concentration resulted in a decrease of thymidine dimer formation of approximately 41%, and tissue treated with *Ugni molinae* at 4% concentration resulted in a decreased formation of thymidine dimer of approximately 25%, as compared to the untreated tissue, thus evidencing their photo-protective effect against UVB-induced DNA damage.

Example 4

In this example, EthniCare® M3 was evaluated to determine its effect on cutaneous erythema (i. e. sunburn). A total of 10 volunteers were recruited, each of which were subjected to mechanically induced erythema caused by the application and removal of transparent medical tape on their forearm for 20 successive repetitions. Erythema measurements were performed using a Mexameter® MX18 and Multiprobe Adapter MPA-5 available from Courage & Khazaka electronic GmbH, of Koln, Germany. An initial measurement was taken immediately after mechanical insult, followed by two additional measurements at intervals of 30 and 60 minutes. The results showed that all of the volunteers treated with EthniCare® M3 experienced a 41% reduction in erythema after 30 minutes, and a 76% reduction in erythema after 60 minutes, thereby evidencing the ability of EthniCare® M3 to soothe skin suffering from externally caused erythema.

These results show that use of EthniCare® M3 provides a soothing action to skin suffering from erythema.

Example 5

In this example, EthniCare® M3 was evaluated to determine its effect on the production of nitric oxide in epidermal keratinocytes in culture. It is well known that the skin's exposure to external aggressors such as UV radiation, pollutants, chemical irritants, aesthetic treatments, and the like can often cause inflammatory reactions, resulting in erythema and edema, both of which are painful and unsightly. One of the factors that signals inflammation is nitric oxide (NO) produced endogenously by a variety of cells in order to regulate physiological processes such as neurotransmission, smooth muscle contractility, platelet reactivity, and cytotoxic activity of immune cells. High levels of NO have been found in pathologies such as rheumatoid arthritis and chronic intestinal inflammation, just to name a few.

Cultured epidermal keratinocytes (PAM 212 keratinocytes) were treated at three concentration levels of EthniCare® M3: 1%, 3%, and 5%. The cultured cells were first caused to express nitric oxide synthase leading to the production of NO from L-arginine. The control was a selective inhibitor of NO synthase, added to the cultured cells that completely (100%) inhibited NO production. NO production was measured using a colorimeter. The results obtained showed that: at 1% EthniCare® M3 inhibited 58.0% of NO production; at 3% it inhibited 46.2%; and at 5% it inhibited 25.3%, evidencing its effectiveness at alleviating skin inflammation.

Example 6

A composition in accordance with the present disclosure was evaluated to determine its ability to successfully pass a micro preservative efficacy testing (PET) challenge. The composition tested is found in Table 2 below.

TABLE 2

| Ingredient | Amount (wt %) |
| --- | --- |
| EthniCare ® M3 | 1.00 |
| *Lactobacillus* ferment | 4.00 |
| *Lactobacillus* and *Cocos nucifera* fruit extract ferment | 2.00 |
| Propanediol | 4.00 |
| Sodium benzoate | 0.30 |
| Potassium sorbate | 0.20 |
| Citric acid | 1.25 |
| Auxiliaries | 23.13 |
| Water | 64.12 |

Figure 4:
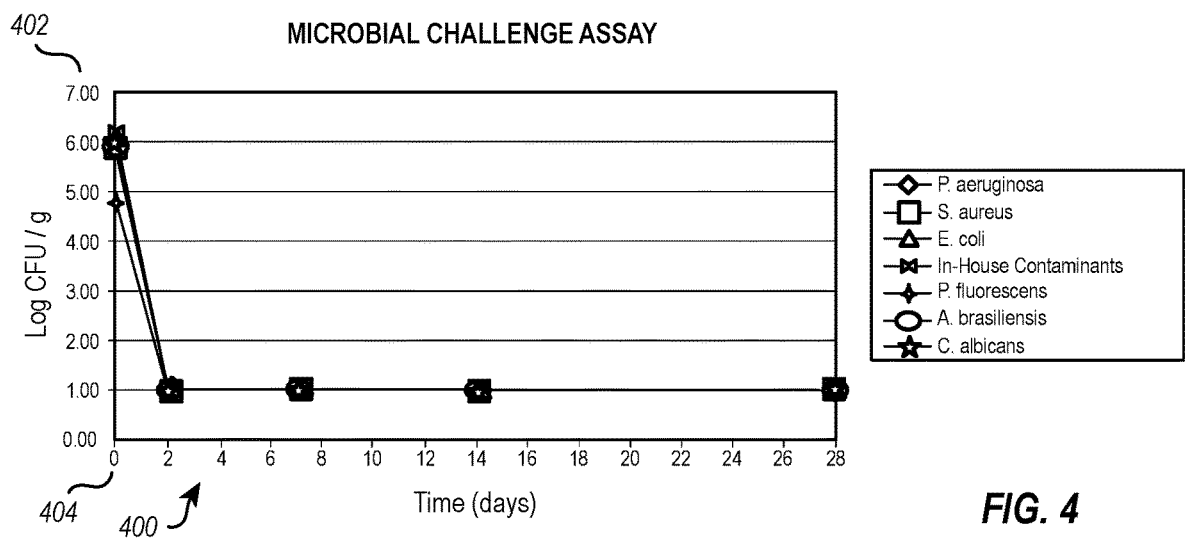
FIG. 4 illustrates the results of a microbial challenge assay using an exemplary all-natural preservative system in a composition according to an embodiment of the disclosure.

A graphical representation of the results of a microbial challenge assay performed for the exemplary skin care composition listed in Table 2 above is illustrated in FIG. 4. As seen in the graph 400 of FIG. 4, which shows the log of colony forming units (CFU)/g sample 402 as a function of days 404 after beginning the microbial challenge assay, the composition reduced each of *Pseudomonas aeruginosa, Staphylococcus aureus, Escherichia coli,* In-House Contaminants, *Pseudomonas fluorescens, Aspergillus brasiliensis,* and *Candida albicans* by day 2, with no subsequent uptick in any of the microbial species. The above test results confirm the successful preservation of the composition using the preservative system of the present disclosure in combination with EthniCare® M3.

Example 7

A composition in accordance with another embodiment the present disclosure was evaluated to determine its ability to successfully pass a micro PET challenge. The composition tested is found in Table 3 below.

TABLE 3

| Ingredient | Amount (wt %) |
| --- | --- |
| EthniCare ® M3 | 2.00 |
| Blend (*Pfaffia paniculata*, *Ptychopetalum olacoides*, and *Lilium candidum* extracts) | 2.00 |
| Propanediol | 4.00 |
| Essential oils | 0.44 |
| Glycerin | 2.00 |
| *Lactobacillus* ferment | 4.00 |
| *Lactobacillus* and *Cocos nucifera* fruit extract ferment | 2.00 |
| Propanediol | 4.00 |
| Sodium benzoate | 0.30 |
| Potassium sorbate | 0.20 |
| Citric acid | 0.15 |
| Auxiliaries | 11.65 |
| Water | 71.26 |

Figure 5:
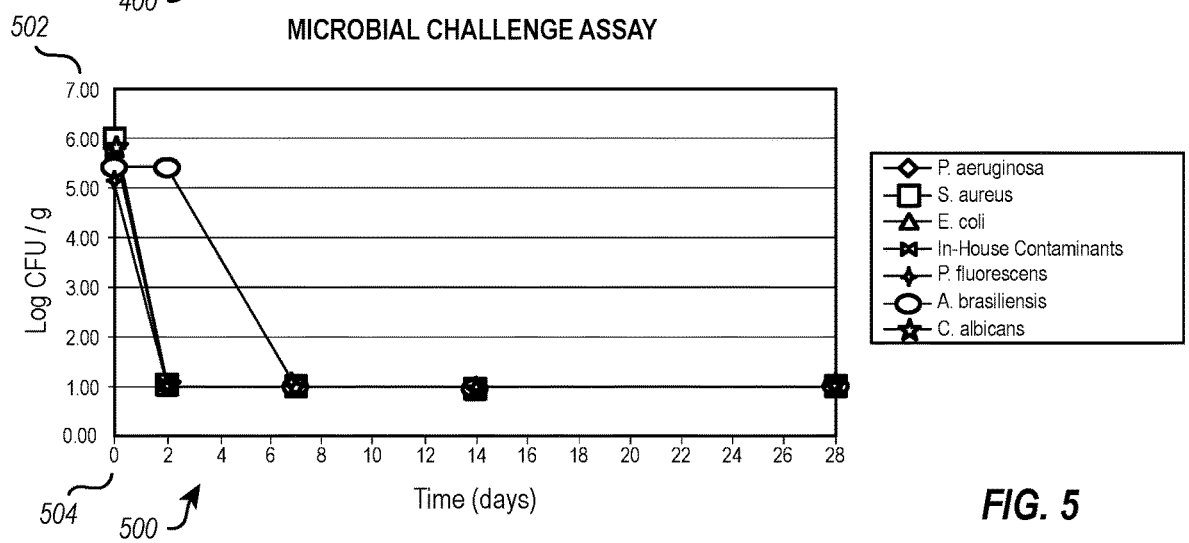
FIG. 5 illustrates the results of a microbial challenge assay using an exemplary all-natural preservative system in a composition according to another embodiment of the disclosure.

As seen in the graph 500 of FIG. 5, which shows the log CFU/g sample 502 as a function of days 504 after beginning the microbial challenge assay, the composition reduced each of *Pseudomonas aeruginosa*, *Staphylococcus aureus*, *Escherichia coli*, In-House Contaminants, *Pseudomonas fluorescens*, and *Candida albicans* by day 2, and *Aspergillus brasiliensis* by day 7, with no subsequent uptick in any of the microbial species. The above test results confirm the successful preservation of the composition using the preservative system of the present disclosure in combination with EthniCare® M3.

Example 8

A composition in accordance with the present disclosure was evaluated to determine its ability to successfully pass a micro (PET) challenge. The composition tested is found in Table 4 below.

TABLE 4

| Ingredient | Amount (wt %) |
| --- | --- |
| EthniCare ® M3 | 2.00 |
| Entadine ® | 2.00 |
| Propanediol | 4.00 |
| Essential oils | 0.34 |
| Glycerin | 2.00 |
| Emollient | 14.00 |
| *Lactobacillus* ferment | 4.00 |
| *Lactobacillus* and *Cocos nucifera* fruit extract ferment | 2.00 |
| Propanediol | 4.00 |
| Sodium benzoate | 0.30 |
| Potassium sorbate | 0.20 |
| Citric acid | 0.15 |
| Auxiliaries | 11.65 |
| Water | 71.26 |

Figure 6:
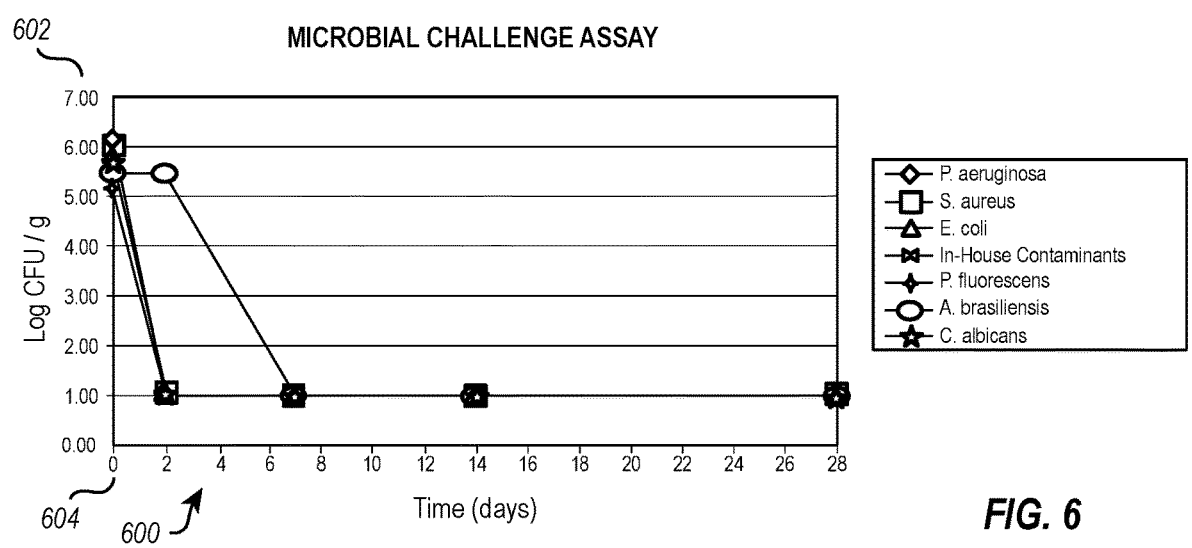
FIG. 6 illustrates the results of a microbial challenge assay using an exemplary all-natural preservative system in a composition according to another embodiment of the disclosure.

As seen in the graph 600 of FIG. 6, which shows the log CFU/g sample 602 as a function of days 604 after beginning the microbial challenge assay, the composition reduced each of *Pseudomonas aeruginosa*, *Staphylococcus aureus*, *Escherichia coli*, In-House Contaminants, *Pseudomonas fluorescens*, and *Candida albicans* by day 2, and *Aspergillus brasiliensis* by day 7, with no subsequent uptick in any of the microbial species. The above test results confirm the successful preservation of the composition using the preservative system of the present disclosure in combination with Ethnicare® M3, Entadine®, and/or other ingredients of a skin care composition for the treatment of oxidative stress according to the embodiments of the present disclosure.

Example 9

The ingredients *Peumus boldus* (Boldo) leaf extract, *Buddleja globosa* (Matico) leaf extract, *Aristotelia chilensis* (Maqui) leaf extract, and *Ugni molinae* (Murta) leaf extract were evaluated to determine what, if any, gene expression effects they may indicate after UVB exposure, per the below-indicated protocol.

Reconstructed Human Epidermis (RHE) tissues were obtained from ZenBio (Research Triangle Park, N.C.; lot#RHE051820) and were used immediately. Tissues were transferred to 6 well plates and were equilibrated for an hour in 1 ml of pre-warmed medium/well ZenSkin provided by the ZenBio. Samples of the above ingredients were then added non-diluted, in triplicates at 3 mg/cm$^2$ with the positive displacement pipette and were spread evenly on top of the RHE tissues. Sterile distilled water was the negative control. Tissues were allowed to incubate for a three-hour period with test materials, afterward were transferred to a new 24 well plate, and exposed to 30 mJ/cm$^2$ (equivalent to 1 minimal erythema dose, or MED) UVB (302 nm) using a Hoefer (Holliston, Mass.) transilluminator. Tissues were then placed back into the original six well plates with medium and allowed to incubate overnight.

At the end of the incubation RNA was extracted and purified with RNeasy Mini Kit cat.#74104 from Qiagen (Germantown, Md.), using a QiaCube Connect robotic station (Qiagen). Purified total RNA was assessed at 260 nm and 280 nm with a Thermo Fisher Scientific (Waltham, Mass.) NanoDrop™ Lite Spectrophotometer.

cDNA was prepared using a High-Capacity RNA-to-cDNA™ Kit (Applied Biosystems, Thermo Fisher) and the expression of the genes of interest was measured by real-time quantitative PCR with a BioRad iCycler iQ Detection System using PCR primers from Realtimeprimers (Elkins Park, Pa.) and AzuraView GreenFast qPCR Blue Mix LR available from Azura Genomics (Raynham, Mass.). Efficiency ΔΔCt method was used for quantification of results, after the normalization of gene expression to HPRT1 and GAPDH (housekeeping genes).

Genes were considered differentially expressed if the p value, as determined by the two-tailed t-test, was ≤0.10 and the modulation was ≥1.8.

Tissues treated with Boldo exhibited an anti-inflammatory (downregulation of CD44, MAP3K7, PTGS2, MMP1, IL8, IL1A; upregulation of TIMP2), anti-apoptotic (downregulation of FOXO3), anti-hyperproliferative (decrease of MAP3K7, PCNA, END1), vasculoprotective (upregulation of HSPG2, ITGB1), and barrier-protective (upregulation of AQP3, TGM1, LOR, downregulation of CD44) response. The decrease of UVB-induced proinflammatory signal by Boldo evidences a reduction in the need for antioxidant response (downregulation of TXNRD1 and perhaps CAT), with no apparent xenobiotic metabolism response.

Tissue treated with Matico decreased the expression of genes coding for late differentiation proteins (IVL, FLG, CDSN) and possibly increased cell survival (BIRC5), evidencing a potential photo-protective effect.

Tissue treated with Maqui showed Maqui to be a highly bioactive substance. It was found to support barrier-protection and ceramide production by way of its strong upregulation of AQP3 and LOR, as well as FLG and GBA, together with a decrease of HAS3 which is expected in differentiated layers of the epithelium and promoted by ascorbic acid, together with anti-inflammatory properties as evidenced by a significant decrease of IL-4, IL-6, and IL-8 activity.

Maqui was also found to trigger a decrease of the expression of AGER, which is the receptor for AGE (advanced glycation endproducts)—a major contributor to skin aging. Maqui also appeared to exhibit pigmentation-inducing effects through the inhibition of ASIP. Other modulated genes include VEGFA (stimulation of blood vessel growth and therefore skin oxygenation), TIMP (MMP inhibition), and TLR2 (upregulation), whose expression is important for repair of insults, such as those caused by UVB irradiation. Maqui-treated tissues also yielded significant amounts of RNA indicative of a broad photo-protective effect of that test material against UVB-induced cytotoxicity which is supported by the strong downregulation of the pro-apoptotic, UVB-induced FOXO3.

Tissue treated with Murta showed a complex bioactivity profile with pro-inflammatory effects (significant increase of IL1A, PTSG2, EDN1) combined with increased expression of genes coding for proteins important for *Stratum corneum* formation (DSG3, TGM1, LOR) and skin repair after UVB irradiation (TLR2). Moreover, CTGF was significantly upregulated showing its potential for increasing ECM (extracellular matrix) production.

Tissue treated with the combination of Matico, Maqui, and Murta exhibited unusually robust bioactivity. Both the VEGFA and PPARD genes were upregulated, evidencing the biologic signaling initiated via the application of the combination of Matico, Maqui, and Murta. This type of immune system related cellular communication is the skin's biological response to environmental stressors. Environmental stressors related to UV radiation exposure can enable oxidative stress and attendant free radical formation on the skin. Similarly, both the IL8 and MT2A genes were down regulated evidencing the triggering of those biological processes of the skin associated with reducing inflammation caused by UV radiation exposure (i.e., anti-inflammatory effect). Lastly, the SMPD1, TGM1 and AQP3 genes were upregulated indicating that the combination triggered a biological process evidencing an enhancement of the skin's barrier function post-UV radiation exposure (i.e., skin priming function).

Example 10

In this example, a composition in accordance with the present disclosure was clinically tested to determine its efficacy in repairing the *Stratum corneum* in order to enhance its barrier function. The composition tested is provided in Table 5 below.

TABLE 5

| Ingredients | Amount (wt %) |
| --- | --- |
| Ethnicare ® M3 | 2.0 |
| Entadine ® | 2.0 |
| Emollient | 14.0 |
| Humectant | 2.1 |
| *Lactobacillus* ferment | 4.0 |
| *Cocos nucifera* fermented and/or mixed with *Lactobacillus* | 2.0 |
| Potassium sorbate | 0.2 |
| 1,3-propanediol | 4.0 |
| Sodium benzoate | 0.3 |
| Emulsifier | 7.4 |
| Purified water | 60.9 |
| Additives | q.s. |
| Total | 100 |

The composition of Example 10 was clinically tested to determine its efficacy in repairing and enhancing the skin barrier. Thirty-four individuals aged 35-64 were asked to apply the composition twice a day at home—once in the morning and once in the evening—under normal use conditions, as a replacement for their normal skin treatment routine. Skin barrier data was collected on day 0 and day 28.

Hydration data was obtained using a corneometer, wherein an increase in coreometer value corresponds to an increase in hydration. The data showed that 79% of test subjects experienced an increase in hydration of more than 11% on day 28. Hence, one of the precursors for skin barrier repair, namely, rehydration of the skin, has successfully been realized.

Next, the barrier repair effect of the composition was determined using an Aquaflux® AF 200 which measures the ability of water to migrate out from the skin barrier and evaporate into the environment, a process known as transepidermal water loss (TEWL). A decrease in TEWL corresponds to a decrease in water loss. The data showed that 74% of test subjects experienced a decrease in TEWL of more than 19% on day 28. A properly functioning skin barrier inhibits excessive water loss which, as can be seen here, has successfully been achieved evidencing skin barrier repair.

The composition of Example 10 was also evaluated to determine its effect on the *Stratum corneum*'s acid mantle and/or skin microbiome based on three parameters that were observed. The first parameter observed was (1) the effect of the composition on the balance between *Staphylococcus epidermidis*, a common commensal bacterium found within the healthy skin microbiome, and *Staphylococcus aureus*, a pathogen carried by roughly half of the population and which is responsible for severe and life-threatening diseases, such as severe sepsis, pneumonia, toxic shocksyndrome, and endocarditis, in addition to the purulent, painful skin infections colloquially known as "boils." *S. epidermidis* is believed to antagonize the growth and/or colonization of *S. aureus* (e.g., through secretion of antimicrobial peptides that target sensitive *S. aureus* strains). Sweating and drying of the skin causes considerable changes to the osmolarity, salt concentration, and pH value of the skin and can affect the balance of these bacteria on the skin. For example, Staphylococci, in general, are resistant to high salt concentrations and can resist changes in osmolarity through expression of genomically-encoded osmoprotectant transport systems and enzymatic conversion systems that allow for the accumulation of osmoprotectants, such as choline or glycine betaine, in the bacterial cells. Yet, the increased frequency of *S. epidermidis* as a colonizer of hydrated and/or undamaged skin, as compared with *S. aureus*, may be due to the increased presence or expression of such protective systems by *S. aureus* and their consequent survival and prevalence on damaged and/or dry skin.

The second parameter observed was (2) the influence the composition had on the biodiversity of key microbes present within the microbiome of the area tested. Finally, the third parameter observed was (3) the influence of the composition on the growth behavior of the key microbes within the microbiome when the composition was in both direct and indirect contact with said microbes.

With regards to the first parameter, a coculture of *S. epidermidis* and *S. aureus* was incubated in the presence of the composition for 4 hours, after which the ratio was measured as compared to a control coculture comprised of approximately 45% *S. epidermidis* and 55% *S. aureus*.

As for the second parameter, a coculture of key microbes comprised of *Propionibacterium acnes, S. epidermidis, Staphylococcus hominis, Staphylococcus capitis, Streptococcus mitis, Corynebacterium simulans*, and *Malassezia globosa* was incubated with the composition for 4 hours, after which the ratio of these bacteria was compared to a control.

Lastly, with regards to the third parameter, the influence of the composition on the growth of said key microbes was determined when the composition was in direct, and indirect, contact with the key microbes.

The results of the above-referenced microbiome tests were evaluated on a scale of 1-3, with 1 indicating no influence or a positive influence (i.e., microbiome friendly), 2 indicating a very weak negative influence (i.e., microbiome neutral), and 3 indicating a clearly negative influence (i.e., microbiome damaging).

The results from this testing yielded an overall grade of 1.9, indicating the composition was microbiome friendly.

Example 11

In this example, a composition in accordance with the present disclosure was clinically tested to determine its efficacy in repairing the *Stratum corneum* to enhance barrier function. The composition tested is provided in Table 6 below.

TABLE 6

| Ingredients | Amount (wt %) |
| --- | --- |
| Ethnicare ® M3 | 1.0 |
| Ssurfactant | 10.1 |
| Emollient | 2.5 |
| Humectant | 3.0 |
| *Lactobacillus* ferment | 4.0 |
| *Cocos nucifera* fermented and/or mixed with *Lactobacillus* | 2.0 |
| Potassium sorbate | 0.2 |
| 1,3-propanediol | 4.0 |
| Sodium benzoate | 0.3 |
| Emulsifier | 4.0 |
| Purified water | 64.1 |
| Additives | q.s. |
| Total | 100 |

The composition of Example 11 was clinically tested in order to determine its efficacy in repairing and enhancing the skin barrier. Thirty-five individuals aged 18-40 were asked to use the composition twice a day at home—once in the morning and once in the evening—under normal use conditions, as a replacement for their normal skin treatment routine. Skin barrier data was collected on day 0 and day 28.

The barrier repair effect of the composition was determined using a Tewameter® TM 300 which measures the ability of water to migrate out from the skin barrier and evaporate into the environment, a process known as transepidermal water loss (TEWL). A decrease in TEWL corresponds to a decrease in water loss (i.e., improved barrier function). The data showed that 57% of test subjects experienced a decrease in TEWL of more than 14% on day 28. A properly functioning skin barrier inhibits excessive water loss which, as can be seen here, has successfully been achieved and evidences skin barrier repair.

Another tool for deducing skin barrier repair is SquameScan® software in conjunction with D-Squame® tape strips. This tool is designed to measure protein content in the *Stratum corneum* using IR-light absorption. A decrease in light absorption corresponds to a decrease in the amount of protein detected, from which one can infer that the skin barrier has experienced a desirable skin restructuring effect—yet another sign of skin barrier repair. The data showed that 80% of test subjects experienced a protein decrease of at least 15% on day 28.

Yet another tool for assessing skin barrier repair is the Courage+Khazaka Sebumeter® SM 810 PC. This device utilizes a photometric method by which a synthetic ribbon that becomes transparent upon contact with sebum/lipids is applied onto a surface of skin to be tested. The greater the amount of sebum absorbed by the ribbon, the more transparent the ribbon becomes. A decrease in Sebumeter® measurement corresponds to a decrease in sebum excreted to the *Stratum corneum* surface. Because an improperly functioning skin barrier typically produces excess sebum, a decrease in sebum production is indicative of skin barrier repair. The data showed that 94% of test subjects experienced at least a 30% decrease in sebum production on day 28.

The composition of Example 11 was also evaluated to determine its effect on the *Stratum corneum*'s acid mantle utilizing the same testing parameters and grading system used in Example 10 above. The results from this testing yielded an overall grade of 1.7, indicating the composition was microbiome friendly.

Example 12

In this example, a composition in accordance with the present disclosure was clinically tested to determine its efficacy in repairing the *Stratum corneum* to enhance barrier function. The composition tested is provided in Table 7 below.

TABLE 7

| Ingredients | Amount (wt %) |
| --- | --- |
| Ethnicare ® M3 | 2.0 |
| Bioskinup ® 3R | 2.0 |
| Emollient | 5.5 |
| Humectant | 2.0 |
| *Lactobacillus* ferment | 4.0 |
| *Cocos nucifera* fermented and/or mixed with *Lactobacillus* | 2.0 |
| Potassium sorbate | 0.2 |
| 1,3-propanediol | 4.0 |
| Sodium benzoate | 0.3 |
| Emulsifier | 2.0 |
| Purified water | 71.3 |
| Additives | Q.s. |
| Total | 100 |

The composition of Example 12 was clinically tested in order to determine its efficacy in repairing and enhancing the skin barrier. Thirty-four individuals aged 35-65 were asked to apply the composition twice a day at home—once in the morning and once in the evening—under normal use conditions, as a replacement for their normal skin treatment routine. Skin barrier data was collected on day 0, day 28, and day 56.

Hydration data was obtained using a corneometer, wherein an increase in coreometer value corresponds to an increase in hydration. The data showed that 90% of test subjects experienced an increase in hydration of more than 18% on day 28, and 71% of test subjects maintained an increase of more than 18% on day 56. Hence, one of the precursors for skin barrier repair, namely, rehydration of the skin, has successfully been realized.

Next, the barrier repair effect of the composition was determined using an Aquaflux® AF 200 which measures TEWL. A decrease in TEWL corresponds to a decrease in water loss. The data showed that 93% of test subjects experienced a decrease in TEWL of at least 33% on day 28, and 97% of test subjects experienced a further decrease in TEWL of at least 44% on day 56. This data clearly evidences that the composition of the present invention not only helps to repair the skin barrier, but that its continued use reinforces the protective capabilities of the barrier by enabling even more water to be retained within the skin. A properly functioning skin barrier inhibits excessive water loss which, as can be seen here, has been achieved evidencing skin barrier repair.

The ability of the composition to increase the thickness of skin as determined by the distance between the skin's dermis and epidermis was determined using a high frequency echograph Dermascan® C 2D instrument which measures dermis and epidermis thickness. An increase in thickness corresponds to a positive skin densifying effect. The data showed that 77% of test subjects experienced an increase in skin thickness of greater than 5% at day 28; and 61% experienced an increase of greater than 2% at day 56, evidencing enhanced barrier functionality.

Skin firmness/elasticity, a marker for skin barrier functionality, was measured using an MPA 580 Cutometer® to ascertain its viscoelastic behavior. The data showed that 65% of test subjects experienced at least an 8% improvement in skin firmness/elasticity at day 28, and 56% experienced at least a 6% improvement in skin firmness/elasticity at day 56. Because skin firmness/elasticity is negatively impacted by an improperly functioning skin barrier, this data evidences an improvement in barrier function based on enhanced firmness/elasticity.

The composition of Example 12 was also evaluated to determine its effect on the *Stratum corneum*'s acid mantle and skin microbiome utilizing the same testing parameters and grading system used in Example 10 above. The results from this testing yielded an overall grade of 1.9, indicating the composition was microbiome friendly.

Example 13

In this example, a composition in accordance with the present disclosure was clinically tested to determine its efficacy in repairing the *Stratum corneum* to enhance its barrier function. The composition tested is provided in Table 8 below.

TABLE 8

| Ingredients | Amount (wt %) |
|---|---|
| Ethnicare ® M3 | 1.0 |
| Emollient | 15.5 |
| humectant | 2.1 |
| *Lactobacillus* ferment | 4.0 |
| *Cocos nucifera* fermented and/or mixed with *Lactobacillus* | 2.0 |
| Potassium sorbate | 0.2 |
| 1,3-propanediol | 4.0 |
| Sodium benzoate | 0.3 |
| emulsifier | 4.5 |
| Purified water | 59.3 |
| additives | q.s. |
| Total | 100 |

The composition of Example 13 was clinically tested in order to determine its efficacy in repairing and enhancing the skin barrier. Thirty-two individuals aged 36-60 were asked to apply the composition twice a day at home—once in the morning and once in the evening—under normal use conditions, as a replacement for their normal skin treatment routine. Skin barrier data was collected on day 0, day 28, and day 56.

Hydration data was obtained using a corneometer, wherein an increase in coreometer value corresponds to an increase in hydration. The data showed that 94% of test subjects experienced an increase in hydration of more than 13% on day 28 and 94% experienced an increase of 19% on day 56. Hence, one of the precursors for skin barrier repair, namely, rehydration of the skin, has successfully been realized.

Next, the barrier repair effect of the composition was determined using an Aquaflux® AF 200 which measures TEWL. A decrease in TEWL corresponds to a decrease in water loss. The data showed that 88% of test subjects experienced a decrease in TEWL of at least 21% on day 28, and 81% experienced a decrease in TEWL of at least 24% on day 56. A properly functioning skin barrier inhibits excessive water loss which, as can be seen here, has successfully been achieved evidencing skin barrier repair.

SquameScan® software in conjunction with D-Squame® tape strips were used to measure protein content in the *Stratum corneum* using IR-light absorption. A decrease in light absorption corresponds to a decrease in the amount of protein detected, thus evidencing that the skin barrier has experienced a desirable skin restructuring effect—yet another sign of skin barrier repair. The data showed that approximately 50% of test subjects experienced a protein decrease of at least 9% on day 28.

Skin firmness/elasticity, a marker for skin barrier functionality, was measured using an MPA 580 Cutometer® to ascertain its viscoelastic behavior. The data showed that 72% of test subjects experienced at least an 8% improvement in skin firmness/elasticity at day 28. Because skin firmness/elasticity is negatively impacted by an improperly functioning skin barrier, this data evidences an improvement in barrier function based on enhanced firmness/elasticity.

The composition of Example 13 was also evaluated to determine its effect on the *Stratum corneum*'s acid mantle and skin microbiome utilizing the same testing parameters and grading system used in Example 10 above. The results from this testing yielded an overall grade of 1.9, indicating the composition was microbiome friendly.

Example 14

In this example, a composition in accordance with the present disclosure, was clinically tested to determine its efficacy in repairing the *Stratum corneum* to enhance its barrier function. The composition tested is provided in Table 9 below.

TABLE 9

| Ingredients | Amount (wt %) |
|---|---|
| Ethnicare ® M3 | 2.0 |
| Bioskinup 3R | 3.0 |
| Emollient | 7.0 |
| Humectant | 2.1 |
| *Lactobacillus* ferment | 4.0 |
| *Cocos nucifera* fermented and/or | 2.0 |

TABLE 9-continued

| Ingredients | Amount (wt %) |
|---|---|
| mixed with *Lactobacillus* | |
| Potassium sorbate | 0.2 |
| 1,3-propanediol | 4.0 |
| Sodium benzoate | 0.3 |
| Emulsifier | 2.0 |
| Purified water | 68.1 |
| Additives | q.s. |
| Total | 100 |

The composition of Example 14 was clinically tested in order to determine its efficacy in repairing and enhancing the skin barrier. Thirty-two individuals aged 35-65 were asked to apply the composition twice a day at home—once in the morning and once in the evening—under normal use conditions, as a replacement for their normal skin treatment routine. Skin barrier data was collected on day 0, day 28, and day 56.

Hydration data was obtained using a corneometer, wherein an increase in coreometer value corresponds to an increase in hydration. The data showed that 100% of test subjects experienced an increase in hydration of more than 29% on day 28 and 97% experienced an increase of at least 35% on day 56. Hence, one of the precursors for skin barrier repair, namely, rehydration of the skin, has successfully been realized.

Next, the barrier repair effect of the composition was determined using an Aquaflux® AF 200 which measures TEWL. A decrease in TEWL corresponds to a decrease in water loss. The data showed that 94% of test subjects experienced a decrease in TEWL of at least 26% on day 28, and 90% experienced a decrease in TEWL of at least 24% on day 56. A properly functioning skin barrier inhibits excessive water loss which, as can be seen here, has successfully been achieved evidencing skin barrier repair.

SquameScan® software in conjunction with D-Squame® tape strips were used to measure protein content in the *Stratum corneum* using IR-light absorption. A decrease in light absorption corresponds to a decrease in the amount of protein detected, thus evidencing that the skin barrier has experienced a desirable skin restructuring effect which is yet another sign of skin barrier repair. The data showed that approximately 47% of test subjects experienced a protein decrease of 6% on day 28, and 61% of those tested experienced an 11% decrease on day 56.

Skin firmness/elasticity, a marker for skin barrier functionality, was measured using an MPA 580 Cutometer® to ascertain its visco-elastic behavior. The data showed that 75% of test subjects experienced an 9% improvement in skin firmness/elasticity at day 28, and 81% of those tested experienced a 10% on day 56. Because skin firmness/elasticity is negatively impacted by an improperly functioning skin barrier, this data evidences an improvement in barrier function based on enhanced firmness/elasticity.

The skin densifying effect of the composition was determined using a high frequency echograph Dermascan® C 2D instrument which measures dermis+epidermis thickness. An increase in thickness corresponds to a positive skin densifying effect. The data showed that 53% of test subjects experienced an increase in skin thickness of greater than 2% at day 28, evidencing enhanced barrier functionality.

The composition of Example 14 was also evaluated to determine its effect on the *Stratum corneum*'s acid mantle/skin microbiome utilizing the same testing parameters and grading system used in Example 10 above. The results from this testing yielded an overall grade of 1.7 indicating the composition was microbiome friendly.

Example 15

In this example, a composition in accordance with the present disclosure was clinically tested to determine its efficacy in repairing the *Stratum corneum* to enhance its barrier function. The composition tested is provided in Table 10 below.

TABLE 10

| Ingredients | Amount (wt %) |
|---|---|
| Ethnicare ® M3 | 2.0 |
| Entadine ® | 2.0 |
| Emollient | 14.0 |
| Humectant | 2.1 |
| *Lactobacillus* ferment | 4.0 |
| *Cocos nucifera* fermented and/or mixed with *Lactobacillus* | 2.0 |
| Potassium sorbate | 0.2 |
| 1,3-propanediol | 4.0 |
| Sodium benzoate | 0.3 |
| Emulsifier | 7.4 |
| Purified water | 60.9 |
| Additives | q.s. |
| Total | 100 |

The composition of Example 15 was clinically tested to determine its ability to inhibit free radical formation, thereby protecting the skin barrier from oxidative damage. Twenty-two individuals aged 20-54 had three separate 4 cm×4 cm areas of their skin analyzed 24 hours after the test: (1) one area where their skin was neither irradiated nor treated; (2) one where their skin was irradiated but not treated; and (3) one where their skin was irradiated and treated. Data evidencing the ability of the composition to inhibit oxidative damage/free radical formation was collected. The device used to irradiate the skin and generate a Minimum Erythema Dose was a Xenon Lamp Solar Light type Monoport 1000W High Power Solar Simulator Model LS 1000, with a radiation spectrum of 290-400 nm (UVA+UVB). All three samples of each test subject's skin were then biochemically analyzed for the presence of squalene peroxide (SQOOH), a biomarker used to evaluate lipid decomposition; superoxide dismutase (SOD), an antioxidant enzyme that protects the body against photo-oxidative damage; catalase (CAT), an enzyme that protects cells against oxidative damage caused by free radicals; and glutathione peroxidase (GPx), a family of enzymes that also protects against oxidative damage. Each of these biomarkers was used to assess the efficacy of the present invention in relation to oxidative stress.

With regards to SQOOH concentration, there was a 44% increase in oxidative stress realized in the irradiated, non-treated skin, as compared to the non-irradiated, non-treated skin. However, with regards to the irradiated and treated skin, there was a 4% reduction in SQOOH concentration in comparison to the irradiated, non-treated skin, evidencing the protective effect of the composition.

As for SOD concentration, there was a 22% increase in oxidative stress realized in the irradiated, non-treated skin, as compared to the non-irradiated, non-treated skin. However, with regards to the irradiated and treated skin, there was a 5% reduction in SOD concentration in comparison to the irradiated, non-treated skin, evidencing the protective effect of the composition.

Regarding CAT concentration, there was a 20% increase in oxidative stress realized in the irradiated, non-treated skin, as compared to the non-irradiated, non-treated skin. However, with regards to the irradiated and treated skin, there was a 5% reduction in CAT concentration in comparison to the irradiated, non-treated skin, evidencing the protective effect of the composition.

And finally, with regards to GPx concentration, there was a 29% increase in oxidative stress realized in the irradiated, non-treated skin, as compared to the non-irradiated, non-treated skin. However, with regards to the irradiated and treated skin, there was a 16% reduction in GPx concentration in comparison to the irradiated, non-treated skin, evidencing the protective effect of the composition.

These biomarker data points clearly establish the protective effect of the composition with regards to free radical-induced oxidative damage.

The composition of Example 15 was also evaluated to determine its effect on the *Stratum corneum*'s acid mantle and skin microbiome utilizing the same testing parameters and grading system used in Example 10 above. The results from this testing yielded an overall grade of 1.9, indicating the composition was microbiome friendly.

The above-discussed in vivo clinical testing clearly establishes, quantitatively, the significant impact on *Stratum corneum* (skin barrier) repair and protection achieved by compositions of the present disclosure.

The above-referenced examples establish the efficacy of the disclosed embodiments to enhance skin damaged by oxidative stress, whether caused by external stressors, i.e., extrinsic factors such as UV radiation and environmental pollution, and/or intrinsic factors such as aging, as well as to prime the skin by repairing and/or protecting its *Stratum corneum* without unduly impairing the *Stratum corneum*'s acid mantle, in order to enhance its barrier function and water retaining capability and thereby allowing it to better defend itself against extrinsic/intrinsic factors and dry-skin-inducing water loss. The embodiments may advantageously comprise one or a combination of a *Peumus boldus* (Boldo) leaf extract, *Buddleja globosa* (Matico) leaf extract, *Aristotelia chilensis* (Maqui) leaf extract, and *Ugni molinae* (Murta) leaf extract, which may synergistically enhance, prime, and/or relieve the skin.

By providing a skin care composition and methods according to the present disclosure, the problem of existing skin care compositions and methods intended for treatment of oxidative stress comprising non-natural ingredients, harsh synthetic preservatives, and other harmful components is addressed. The embodiments of the present disclosure advantageously provide a composition effective for neutralizing free radicals in the skin and/or priming the skin by repairing and/or protecting its *Stratum corneum* without impairing the *Stratum corneum*'s acid mantle, in order to enhance its ability to defend itself against future free-radical aggression and dry skin-inducing water loss.

The skin care composition and method embodiments address the problem of existing skin care treatment modalities being non-natural and/or being inadequate for treating skin conditions such as oxidative stress.

What is claimed is:

1. A composition for application onto human skin, the composition comprising:
   (1) a mixture of at least:
      (a) about 1 to about 10% by weight of a leaf extract of *Aristotelia chilensis;*
      (b) about 0.5 to about 3% by weight of a leaf extract of *Buddleja globosa;*
      (c) about 0.5 to about 3% by weight of a leaf extract of *Ugni molinae;*
      (d) optionally, about 1 to about 5% by weight of a bark/seed extract of *Entada phaseoloides;*
      (e) optionally, about 1 to about 5% by weight of a blend of *Pfaffia paniculata, Ptychopetalum olacoides*, and *Lilium candidum* extracts; and
      (f) about 1.0 to about 8.0% by weight of at least one humectant;
   (2) an emulsifier; and
   (3) a dermatologically acceptable carrier,
   wherein (a)-(f) synergistically neutralize existing free radicals present in the skin, while proactively priming the skin by repairing and/or protecting its stratum corneum without unduly impairing the *Stratum corneum*'s acid mantle,
   wherein the composition is natural, free of a skin-sensitizing amount of an essential oil, and has a pH ranging from about 4.5 to about 5.5 and
   wherein the composition is in the form of a solution, suspension, lotion, cream, gel, spray, ointment, foam, serum, or combination thereof.

2. The composition of claim 1, wherein (a) is employed in an amount of from about 1 to about 10% by weight, (b) is employed in an amount of from about 0.5 to about 3% by weight, (c) is employed in an amount of from about 0.5 to about 3% by weight, (d) is employed in an amount of from about 1 to about 5% by weight, and (f) is employed in an amount of from about 1.0 to about 6.0% by weight, all weights based on the total weight of the composition.

3. The composition of claim 1, wherein (a) is employed in an amount of from about 1 to about 10% by weight, (b) is employed in an amount of from about 0.5 to about 3% by weight, (c) is employed in an amount of from about 0.5 to about 3% by weight, (e) is employed in an amount of from about 1 to about 5% by weight, and (f) is employed in an amount of from about 1.0 to about 6.0% by weight, all weights based on the total weight of the composition.

4. The composition of claim 1, further comprising Peumus boldus leaf extract employed in an amount from about 0.1 to about 5% by weight based on the total weight of the composition.

5. A composition intended for application onto human skin, the composition comprising:
   (1) a preservative system comprising:
      (a) from about 1 to about 5% by weight of a *Lactobacillus* ferment;
      (b) from about 1 to about 5% by weight, of a *Lactobacillus* and *Cocos nucifera* fruit extract;
      (c) up to about 0.5% by weight of salicylic acid;
      (d) from about 0.1 to about 0.5% by weight of at least one salt of a weak acid; and
      (e) from about 1 to about 10% by weight of a petroleum-free 1,3-propanediol;
   (2) a mixture of at least:
      (f) about 1 to about 10% by weight of a leaf extract of *Aristotelia chilensis;*
      (g) about 0.5 to about 3% by weight of a leaf extract of *Buddleja globosa;*
      (h) about 0.5 to about 3% by weight of a leaf extract of *Ugni molinae;*
      (i) optionally, about 1 to about 5% by weight of a bark/seed extract of *Entada phaseoloides;*
      (j) optionally, about 1 to about 5% by weight of a blend of *Pfaffia paniculata, Ptychopetalum olacoides*, and *Lilium candidum* extracts; and (k) about 1.0 to about 8.0% by weight of at least one humectant, wherein (f) (k) synergistically neutralize existing free radicals present in the skin while proactively priming the skin by repairing and/or protecting its stratum corneum without unduly impairing the *Stratum corneum*'s acid mantle;

(3) an emulsifier; and (4) a dermatologically acceptable carrier, wherein the composition is natural, free of a skin sensitizing-effective amount of an essential oil, and has a pH ranging from about 4.5 to about 5.5.

6. The composition of claim 5, wherein (a) is employed in an amount of from about 2 to about 4% by weight, (b) is employed in an amount of from about 2 to about 4% by weight, (c) is employed in an amount of from about 0.1 to about 0.45% by weight, and (d) is employed in an amount of from about 0.2 to about 0.4% by weight, and (e) is employed in an amount of from about 2 to about 8% by weight, all weights based on the total weight of the composition.

7. The composition of claim 5, wherein (f) is employed in an amount of from about 1 to about 10% by weight, (g) is employed in an amount of from about 0.5 to about 3% by weight, (h) is employed in an amount of from about 0.5 to about 3% by weight, (i) is employed in an amount of from about 1 to about 5% by weight, (j) is employed in an amount of from about 1 to about 5% by weight, and (k) is employed in an amount of from about 1.0 to about 6.0% by weight, all weights based on the total weight of the composition.

8. The composition of claim 5, wherein (f) is employed in an amount of from about 2 to about 5% by weight, (g) is employed in an amount of from about 1 to about 2% by weight, (h) is employed in an amount of from about 1 to about 2% by weight, (i) is employed in an amount of from about 2 to about 3% by weight, (j) is employed in an amount of from about 2 to about 3% by weight, and (k) is employed in an amount of from about 1.5 to about 4.0% by weight, all weights based on the total weight of the composition.

9. The composition of claim 5, wherein (f)is employed in an amount of from about 2 to about 5% by weight, (g) is employed in an amount of from about 1 to about 2% by weight, (h) is employed in an amount of from about 1 to about 2% by weight, (i) is employed in an amount of from about 2 to about 3% by weight, and (k) is employed in an amount of from about 2.0 to about 6.0% by weight, all weights based on the total weight of the composition.

10. The composition of claim 5, having a pH ranging from about 4.8 to about 5.3.

11. The composition of claim 5, further comprising Peumus boldus leaf extract employed in an amount of from about 0.1 to about 5% by weight, based on the total weight of the composition.

12. A method of simultaneously treating skin damaged by oxidative stress and proactively priming the skin in order to enhance its ability to defend itself against free radical aggression and dry-skin-inducing water loss, comprising applying onto the skin the composition of claim 1.

13. The method of claim 12, wherein (a) is employed in an amount of from about 1 to about 10% by weight, (b) is employed in an amount of from about 0.5 to about 3% by weight, (c) is employed in an amount of from about 0.5 to about 3% by weight, (d) is employed in an amount of from about 1 to about 5% by weight, and (f) is employed in an amount of from about 1.0 to about 6.0% by weight, all weights based on the total weight of the composition.

14. A method of simultaneously treating skin suffering from oxidative stress and proactively priming the skin in order to enhance its ability to defend itself against future free radical aggression and dry-skin-inducing water loss by applying onto the skin the composition of claim 5.

* * * * *